(12) United States Patent
Breyen et al.

(10) Patent No.: US 9,724,524 B2
(45) Date of Patent: Aug. 8, 2017

(54) INTERCONNECTION OF CONDUCTOR TO FEEDTHROUGH

(75) Inventors: Mark Breyen, Champlin, MN (US); Tom Miltich, Otsego, MN (US); Gordon Munns, Stacy, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 175 days.

(21) Appl. No.: 13/196,698

(22) Filed: Aug. 2, 2011

(65) Prior Publication Data

US 2013/0035733 A1 Feb. 7, 2013

(51) Int. Cl.
| A61N 1/00 | (2006.01) |
| A61N 1/375 | (2006.01) |
| B23K 35/30 | (2006.01) |
| B23K 35/32 | (2006.01) |
| B23K 101/38 | (2006.01) |

(52) U.S. Cl.
CPC ........ *A61N 1/3754* (2013.01); *B23K 35/3013* (2013.01); *B23K 35/322* (2013.01); *B23K 2201/38* (2013.01); *Y10T 29/49149* (2015.01)

(58) Field of Classification Search
CPC .............. A61N 1/3754; B23K 2201/38; B23K 35/3013; B23K 35/322; Y10T 29/49149
USPC .................................................... 607/36–37
See application file for complete search history.

(56) References Cited

U.S. PATENT DOCUMENTS

| 5,434,358 A | 7/1995 | Glahn et al. |
| 5,559,056 A | 9/1996 | Weiler |
| 5,620,476 A * | 4/1997 | Truex et al. ................... 607/36 |
| 5,782,891 A * | 7/1998 | Hassler et al. ................. 607/36 |
| 5,817,984 A * | 10/1998 | Taylor ................. H01B 17/305 174/152 GM |
| 5,855,995 A | 1/1999 | Haq et al. |
| 6,059,601 A | 5/2000 | Hirai et al. |
| 6,414,835 B1 | 7/2002 | Wolf et al. |
| 6,516,808 B2 | 2/2003 | Schulman |
| 6,586,675 B1 | 7/2003 | Bealka et al. |
| 6,618,623 B1 * | 9/2003 | Pless ...................... A61N 1/375 607/116 |
| 6,765,780 B2 * | 7/2004 | Brendel et al. ............... 361/302 |

(Continued)

FOREIGN PATENT DOCUMENTS

| EP | 1688160 A2 | 8/2006 |
| JP | 05-334911 | 12/1993 |

(Continued)

OTHER PUBLICATIONS

International Search Report/Written Opinion for Application No. PCT/US2012/048870 mailed Nov. 12, 2012 (16 pages).

(Continued)

*Primary Examiner* — Lindsey G Wehrheim
(74) *Attorney, Agent, or Firm* — Foley & Lardner LLP

(57) ABSTRACT

A method of interconnecting a conductor and a hermetic feedthrough of an implantable medical device includes welding a lead to a pad on a feedthrough. The feedthrough includes a ceramic insulator and a via hermetically bonded to the insulator. The via includes platinum. The pad is bonded to the insulator and electrically connected to the via, includes platinum, and has a thickness of at least 50 μm. The lead includes at least one of niobium, platinum, titanium, tantalum, palladium, gold, nickel, tungsten, and oxides and alloys thereof.

16 Claims, 22 Drawing Sheets

(56) References Cited

U.S. PATENT DOCUMENTS

| | | | |
|---|---|---|---|
| 7,164,572 B1* | 1/2007 | Burdon et al. | 361/302 |
| 7,174,223 B2 | 2/2007 | Dalton et al. | |
| 7,187,974 B2* | 3/2007 | Haeg et al. | 607/36 |
| 7,191,009 B2* | 3/2007 | Laske et al. | 607/37 |
| 7,211,103 B2 | 5/2007 | Greenberg | |
| 7,310,216 B2* | 12/2007 | Stevenson et al. | 361/302 |
| 7,630,768 B1 | 12/2009 | Coffed et al. | |
| 7,668,597 B2* | 2/2010 | Engmark et al. | 607/37 |
| 7,988,507 B2 | 8/2011 | Darley et al. | |
| 8,000,804 B1 | 8/2011 | Wessendorf et al. | |
| 8,160,707 B2* | 4/2012 | Iyer et al. | 607/37 |
| 8,494,636 B2 | 7/2013 | Smith et al. | |
| 2002/0166618 A1* | 11/2002 | Wolf et al. | 156/89.12 |
| 2003/0082958 A1 | 5/2003 | Robinson et al. | |
| 2004/0068302 A1 | 4/2004 | Rodgers et al. | |
| 2004/0116976 A1 | 6/2004 | Spadgenske | |
| 2004/0267107 A1 | 12/2004 | Lessar et al. | |
| 2006/0247734 A1 | 11/2006 | Greenberg et al. | |
| 2006/0259093 A1 | 11/2006 | Stevenson et al. | |
| 2006/0282126 A1 | 12/2006 | Fischbach et al. | |
| 2006/0283624 A1 | 12/2006 | Ok et al. | |
| 2007/0041164 A1 | 2/2007 | Greenberg et al. | |
| 2007/0060969 A1 | 3/2007 | Burdon et al. | |
| 2007/0060970 A1 | 3/2007 | Burdon et al. | |
| 2007/0096281 A1 | 5/2007 | Greenberg et al. | |
| 2007/0179553 A1 | 8/2007 | Iyer et al. | |
| 2007/0179554 A1* | 8/2007 | Iyer et al. | 607/37 |
| 2007/0217121 A1 | 9/2007 | Fu et al. | |
| 2007/0236861 A1 | 10/2007 | Burdon et al. | |
| 2008/0208289 A1 | 8/2008 | Darley et al. | |
| 2008/0269623 A1 | 10/2008 | Ruben | |
| 2008/0314502 A1 | 12/2008 | Ok et al. | |
| 2009/0079518 A1* | 3/2009 | Iyer | 333/182 |
| 2009/0236141 A1 | 9/2009 | Kim et al. | |
| 2011/0029036 A1 | 2/2011 | Yamamoto et al. | |
| 2011/0041330 A1 | 2/2011 | Kumar et al. | |
| 2011/0048770 A1 | 3/2011 | Reiterer et al. | |
| 2011/0106228 A1* | 5/2011 | Reiterer | A61N 1/3754 607/115 |
| 2011/0226304 A1 | 9/2011 | Hayashi et al. | |

FOREIGN PATENT DOCUMENTS

| | | |
|---|---|---|
| JP | 2010-109069 | 5/2010 |
| JP | 2010-177482 | 8/2010 |
| JP | 2011-091411 | 5/2011 |
| WO | WO 97/38752 A2 | 10/1997 |
| WO | WO 2005/007718 A1 | 1/2005 |
| WO | WO-2010/141100 A1 | 12/2010 |
| WO | WO-2011/025667 | 3/2011 |
| WO | WO 2011/025667 A1 | 3/2011 |

OTHER PUBLICATIONS

Communication from USPTO regarding Third Party Submission under 37 C.F.R. 1.290 regarding U.S. Appl. No. 13/196,683 (mailed Sep. 19, 2013).

Third Party Submission under 37 C.F.R. 1.290 regarding U.S. Appl. No. 13/196,683 (submitted Sep. 17, 2013).

The Office Action issued in Chinese Patent Application No. 201280048405.1, dated Jun. 1, 2016.

The Chinese office action issued in Chinese patent app. No. 201410345106.5, dated Jan. 5, 2016.

\* cited by examiner

INTERCONNECTION OF CONDUCTOR TO FEEDTHROUGH

BACKGROUND

Technology disclosed herein relates generally to the field of feedthroughs serving as an electrical interface to connect portions of a circuit on opposite sides of a barrier. More specifically, technology disclosed herein relates to hermetic feedthroughs for use with implantable medical devices that are both biocompatible and biostable over a long duration.

SUMMARY

One exemplary embodiment relates to a method of interconnecting a conductor and a hermetic feedthrough of an implantable medical device. The method includes welding a lead to a pad on a feedthrough. The feedthrough includes a ceramic insulator and a via hermetically bonded to the insulator. The pad has a thickness of at least 50 µm and is bonded to the insulator and electrically connected to the via. The via and pad include platinum and the lead includes at least one material selected from the group consisting of niobium, platinum, titanium, tantalum, palladium, gold, nickel, tungsten, and oxides and alloys thereof.

Another exemplary embodiment relates to a method of interconnecting a conductor and feedthrough, which includes joining a lead to a pad on a feedthrough using a laser. The feedthrough includes a ceramic insulator and a via hermetically bonded to the insulator. The pad has a thickness of at least 50 µm and is hermetically bonded to the insulator and electrically connected to the via. The via and pad include platinum and the lead includes at least one of niobium, platinum, titanium, tantalum, palladium, gold, nickel, tungsten, and oxides and alloys thereof.

Yet another exemplary embodiment relates to a feedthrough system for an implantable medical device. The feedthrough system includes an insulator, a via hermetically bonded to the insulator, a pad bonded to the insulator and electrically connected to the via on an outside surface of the insulator and the via, and a lead fastened to the pad. The pad is substantially centered over the via and has a thickness of at least 50 µm. The insulator is formed from a ceramic material, the via includes platinum, and the pad includes platinum. The lead includes at least one material selected from the group consisting of niobium, platinum, titanium, tantalum, palladium, gold, nickel, and oxides and alloys thereof.

Still another exemplary embodiment relates to an implantable medical device, which includes a ferrule configured to support an insulator of a feedthrough. The ferrule includes a frame configured to surround sides of the insulator. The frame includes an outer extension, configured to be fastened to an encasement of the implantable medical device, and an interior surface configured to face the insulator. The interior surface is at least one of (i) flat and only faces ends and lengthwise sides of the insulator without extending over a top or bottom of the insulator; or (ii) mostly flat and only faces ends and lengthwise sides of the insulator except for further including two or more tabs that project from the mostly flat surface to receive a top or bottom of the insulator.

DETAILED DESCRIPTION

Before turning to the figures, which illustrate various exemplary embodiments in detail, it should be understood that the present application is not limited to the details or methodology set forth in the description or illustrated in the figures. It should also be understood that the terminology is for the purpose of description only and should not be regarded as limiting.

Figure 1:
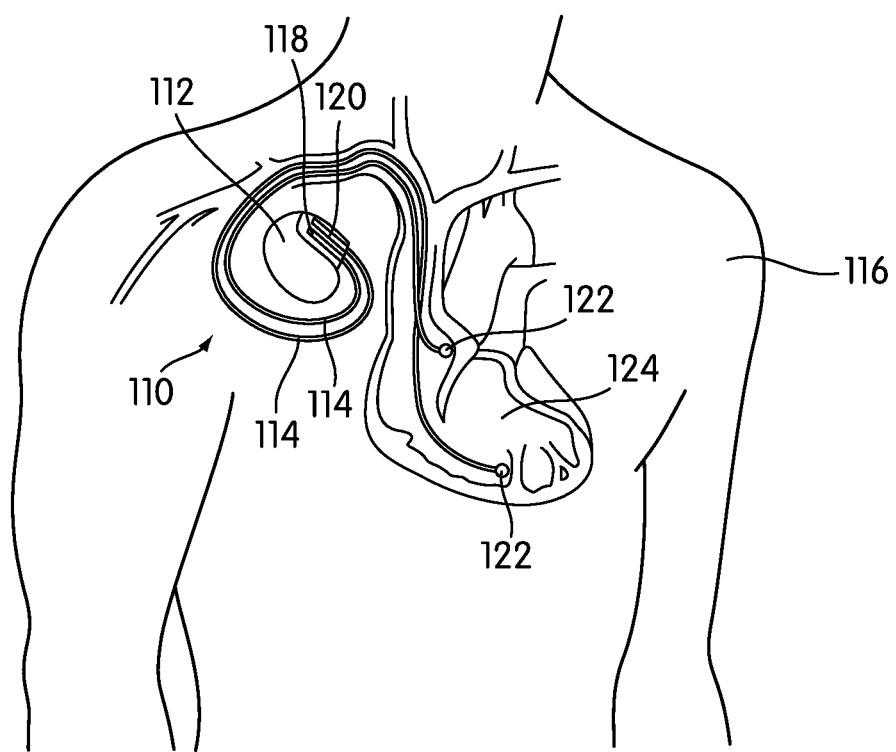
FIG. 1 is a schematic view of a medical device implanted within a patient according to an exemplary embodiment.

Referring to FIG. 1, an implantable medical device 110, such as a pacemaker or a defibrillator, includes a base 112 (e.g., pulse generator, main body) and leads 114. The device 110 may be implanted in a human patient 116 or other being. In some embodiments, the device 110 is configured to provide a therapeutic treatment in the form of an electrical pulse, which in some embodiments may be on the order of about 700 volts. In contemplated embodiments, the device 110, or a variation thereof, may be used to treat or monitor a wide range of conditions such as pain, incontinence, hearing loss, movement disorders including epilepsy and Parkinson's disease, sleep apnea, cardiac rhythm morbidities, and a variety of other physiological, psychological, and emotional conditions and disorders.

Within the base 112, the device 110 may include components, such as control circuitry and energy storage devices (e.g., one or more batteries, capacitors, etc.), that may not be biocompatible or able to function when wet. However, according to an exemplary embodiment, the base 112 is hermetically-sealed and formed with an exterior of a biocompatible and biostable material (e.g., a titanium, biocompatible coating) isolating the interior of the base 112 from bodily fluids of the patient 116 that are outside the base 112. In some embodiments, the base 112 further includes a hermetic feedthrough 118 (e.g., through-connection, interface, connector, coupling) formed from or including an exterior of a biocompatible and biostable material. The feedthrough 118 facilitates electric transmission through the base 112, from the interior of the base 112 to the exterior of the base 112 and vice versa.

By way of example, during use of the implantable medical device 110, a charge stored in a capacitor within the base 112 may be discharged in the form of an electrical pulse. The electrical pulse is transferred through a wall of the base 112 via the feedthrough 118. The electrical pulse is then received by at least one of the proximal ends 120 of the leads 114 and transmitted via conductive pathways through at least one of the leads 114 to electrodes 122, which may be located at distal ends of the leads 114. The electrodes 122 may be coupled to a heart 124 or other part(s) of the patient 116 to promote a pattern of heartbeats, stimulate heartbeats, sense heartbeats, promote healing, or for other reasons.

In some embodiments, activity is sensed via the electrodes 122 and communicated by the leads 114 to control circuitry in the base 112 via the feedthrough 118. The sensed activity may be used as feedback by the control circuitry to manage the operation of the device 110 and/or to optimize the therapy delivered to the patient. In still other embodiments, the feedthrough 118 may also be used to facilitate transfer of electricity to the energy storage device within the base 112, such as for recharging or testing. In other embodiments, other energy storage devices may be used, such as a hybrid system using a combination of one or more batteries and capacitors for energy storage. According to an exemplary embodiment, two or more leads may be coupled to the interior of the base 112 via the feedthrough 118. In other embodiments, a single lead may be used (see generally device 210 as shown in FIG. 2).

Figure 2:
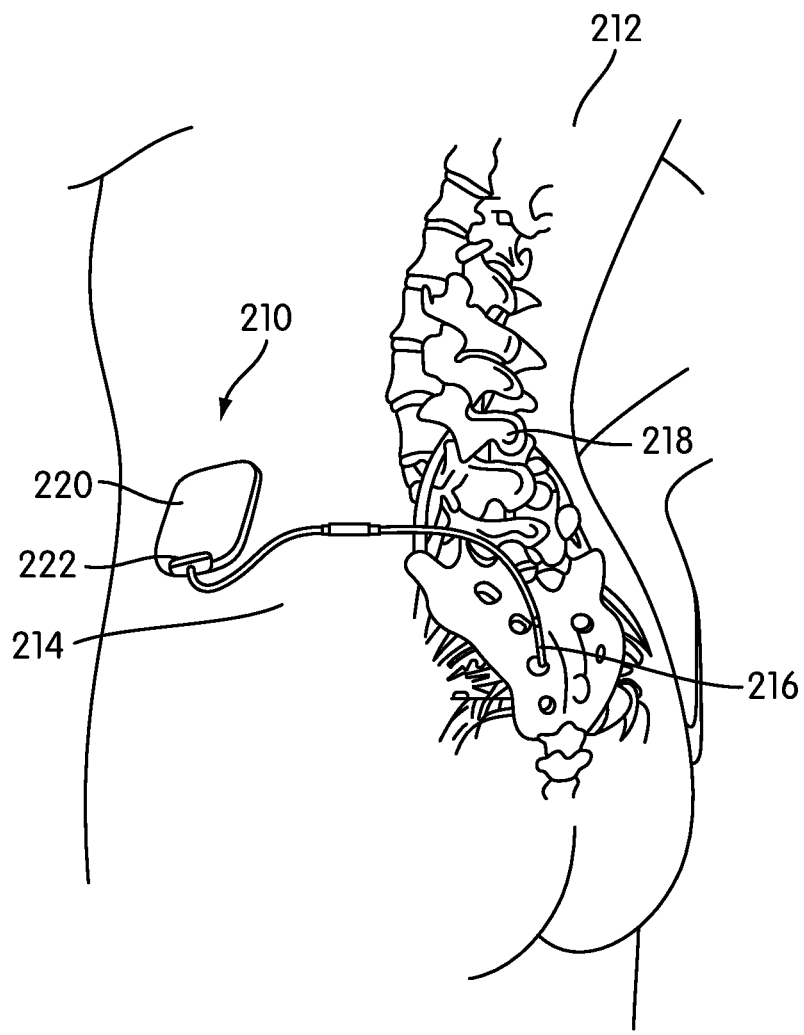
FIG. 2 is schematic view of another medical device implanted within a patient according to an exemplary embodiment.

Referring to FIG. 2, an implantable medical device 210 (e.g., electrical stimulator, monitoring loop recorder, neurostimulator, or other type of implantable medical device) is configured to influence a nervous system and/or organs of a patient 212. The device 210 may be implanted, for example, into a subcutaneous pocket in an abdomen 214, pectoral region, upper buttocks, or other area of the patient 212, and the device 210 may be programmed to provide a stimulation signal (e.g., electrical pulse, frequency, voltage) associated with a specific therapy. During use, electrical contacts integrated with a lead 216 are placed at a desired stimulation site, such as a portion of a spine 218 or brain. The lead 216 is also connected to a base 220 of the device 210 by way of a feedthrough 222 integrated with an exterior surface of the base 220. In some contemplated embodiments, a feedthrough can transmit therapy and/or send signals directly to electrodes mounted on the implantable medical device (e.g., so-called leadless devices).

According to an exemplary embodiment, the feedthrough 222, as well as the rest the exterior of the base 220, is designed to be hermetically sealed, biocompatible, and biostable in order to prevent leakage of bodily fluids to the interior of the base 220, as well as to prevent leakage from the interior of the base 220 into the body during the implant duration of the implantable medical device 210. According to an exemplary embodiment, the feedthrough 222 is hermetically sealed, and remains hermetically sealed when implanted in the body, displaying long-term biostability on the order of years, such as at least a year, five years, ten years, twenty years, or more.

Standard testing, such as in-vitro highly-accelerated immersion testing for hermeticity and dye infiltration, may be used to provide a reliable indicator of the ability of the feedthroughs 118, 222 to remain hermetically sealed and biostable when implanted over an extended period. Long-term hermeticity and/or biostability may be demonstrated by the occurrence of substantially no dye infiltration and substantially no loss of the hermetic seal (i.e., evidenced by the absence of dye penetration, helium leak, etc.) through the feedthrough after immersion in simulated body fluid at a controlled temperature (e.g., 120° C., 150° C., 200° C. or more) and pressure (e.g., 1.5 atm, 3.5 atm) over an extended test duration (e.g., 48 hours, 72 hours, 96 hours, a month or more), while maintaining high electrical conductivity through the feedthrough 222. Other standard tests, such as a Helium leak test and a 3-point bending strength test, may also evidence long-term biostability, as may be indicated by minimal degradation of strength and retention of low Helium leak rates, typically less than $1\times10^{-8}$ atm-cc He per second (e.g., less than $5\times10^{-9}$ atm-cc He per second).

Although described herein with respect to particular implantable medical devices, it should be understood that the concepts disclosed herein may be utilized in conjunction with a wide range of implantable medical devices, such as pacemakers, implantable cardioverter-defibrillators, sensors, cardiac contractility modulators, cardioverters, drug administering devices, diagnostic recorders, cochlear implants, and other devices. According to still other contemplated embodiments, devices other than implantable medical devices may also benefit from the concepts disclosed herein.

Figure 3:
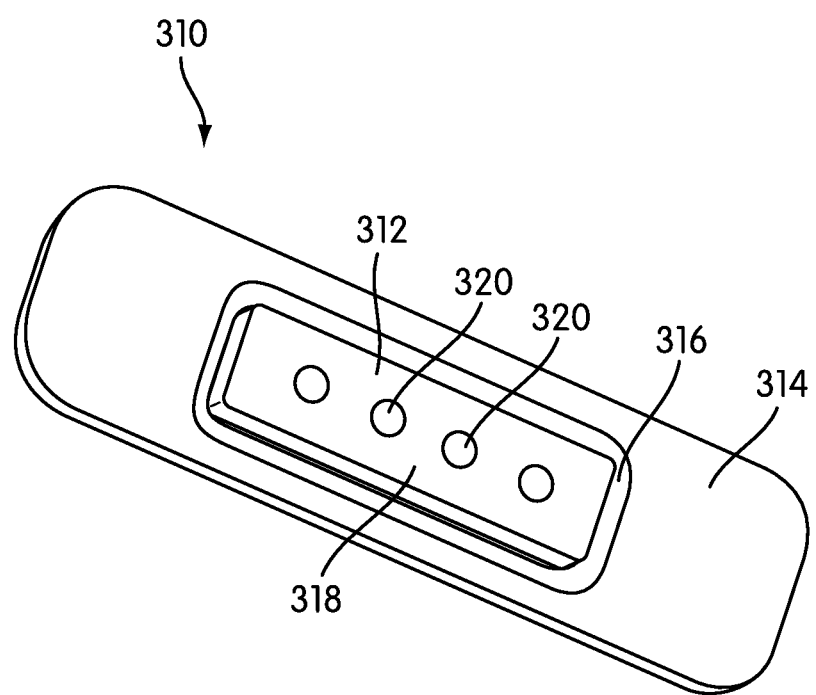
FIG. 3 is a perspective view of a portion of a medical device including a feedthrough according to an exemplary embodiment.

Referring now to FIG. 3, a wall 310 or encasement structure of an implantable medical device (see, e.g., implantable medical devices 110 and 210 as shown in FIGS. 1-2) includes a feedthrough 312. The feedthrough 312 is fastened to a portion 314 of the wall 310, such as a ferrule, in a recess 316 of the wall 310 that is configured to receive the feedthrough 312. The wall 310 may be integrated with another wall or walls to form a biocompatible, hermetically-sealed exterior for a base (see, e.g., bases 112 and 220 as shown in FIGS. 1-2) of the implantable medical device. In other embodiments, a ferrule does not include a recess. In still other embodiments, a feedthrough may be integrated directly into a wall, without use of a ferrule.

According to an exemplary embodiment, the feedthrough 312 is primarily formed from a material 318 that is generally electrically non-conductive, such as an insulator or a dielectric material. The feedthrough further includes one or more conduits 320 (e.g., conductive member, vertical interconnect access (via), path, pathway) that are generally electrically conductive and that extend through the material 318 of the feedthrough 312 that is generally electrically non-conductive. In some contemplated embodiments, the conduits 320 are integrated with the material 318 but do not extend through the material 318, and instead extend along a surface of the material 318, or on the surface of an intermediary material between the conduits 320 and the surface of the material 318. In this manner, the electrical signal can be conducted in a horizontal direction between conductive conduits (e.g., vias) or external pads, or otherwise connecting internal and/or external points that are laterally disposed from one another.

Figure 4:
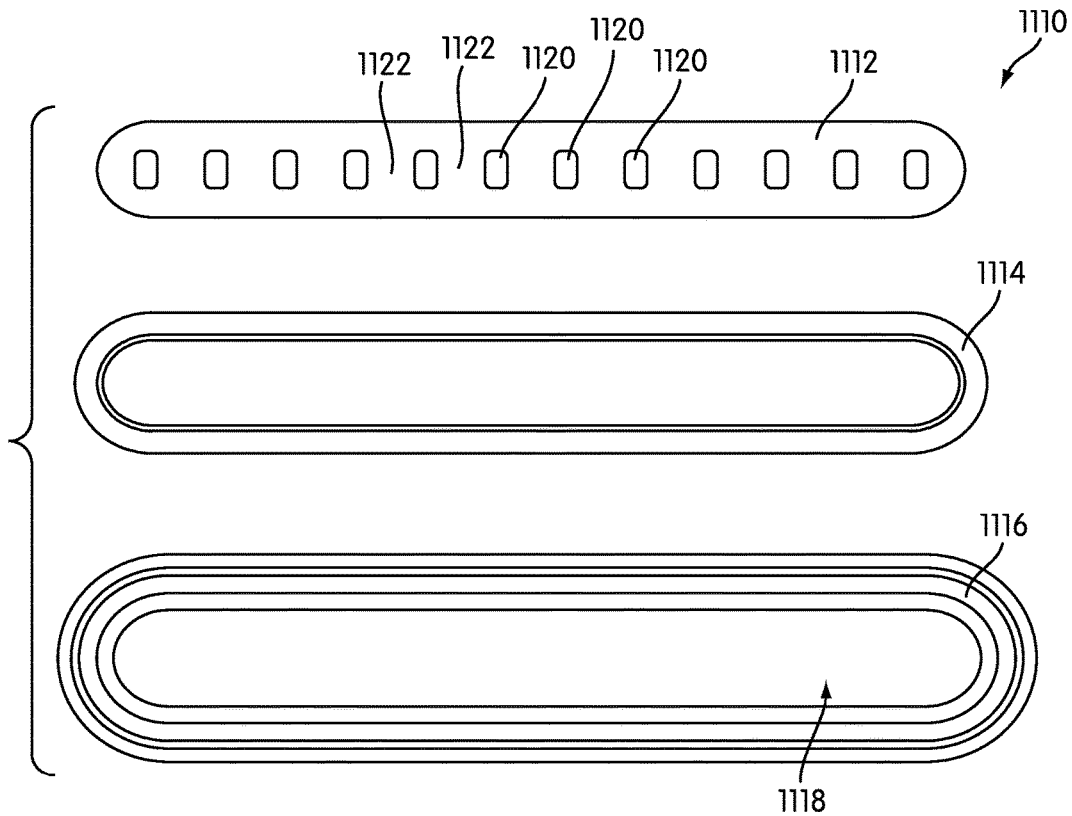
FIG. 4 is a top view of components of a medical device according to another exemplary embodiment.
Figure 5:
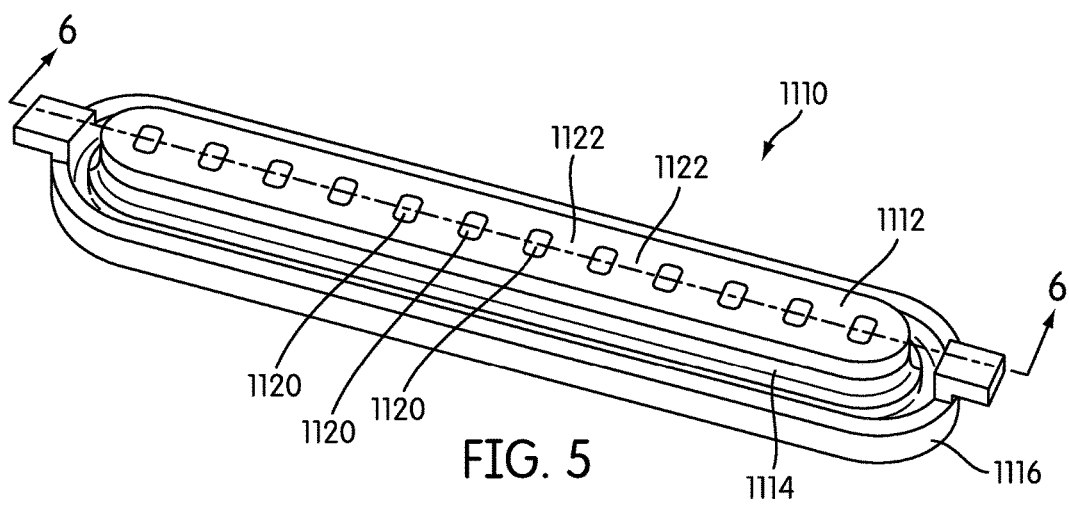
FIG. 5 is a perspective view of the portion of the medical device of FIG. 4.

Referring to FIGS. 4-5, components of an implantable medical device 1110 include a feedthrough 1112 (e.g., co-fired ceramic, monolith), a ring 1114 of filler material for brazing, and a ferrule 1116. During assembly of the implantable medical device 1110, the feedthrough 1112 is inserted into a recess 1118 (e.g., opening) in the ferrule 1116, the ring 1114 is then melted and brazed between the feedthrough 1112 and the ferrule 1116. In some embodiments, the ring 1114 is a gold ring, and the ferrule 1116 is formed from titanium. Gold and titanium are used in some embodiments due to the associated biocompatible properties and relative melting temperatures. In some embodiments, side walls of the ceramic insulator are coated (e.g., by a variety of potential methods, such as physical vapor deposition, sputtering, electron-beam evaporation, plating, chemical vapor deposition) with a metal, such as niobium, titanium, molybdenum, or other biocompatible materials, to facilitate joining between the insulator and the ferrule. The coat of metal may facilitate adhesion and brazing of a pre-form gold ring to join the insulator and ferrule. In other contemplated embodiments, a ring and ferrule are formed from different materials or combinations of materials.

Figure 6:
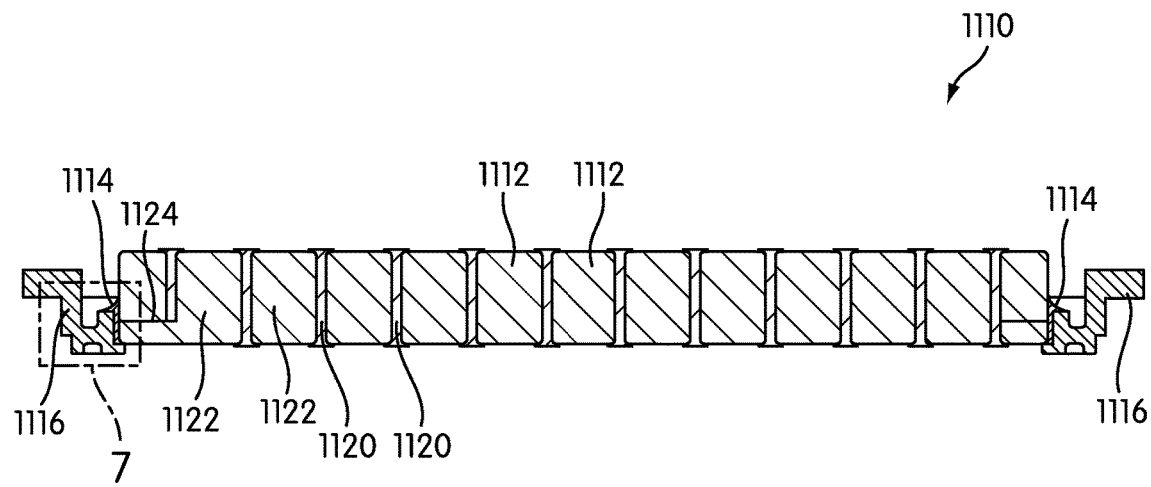
FIG. 6 is a sectional view of the portion of the medical device of FIG. 4, taken along line 6-6 as shown in FIG. 5.
Figure 7:
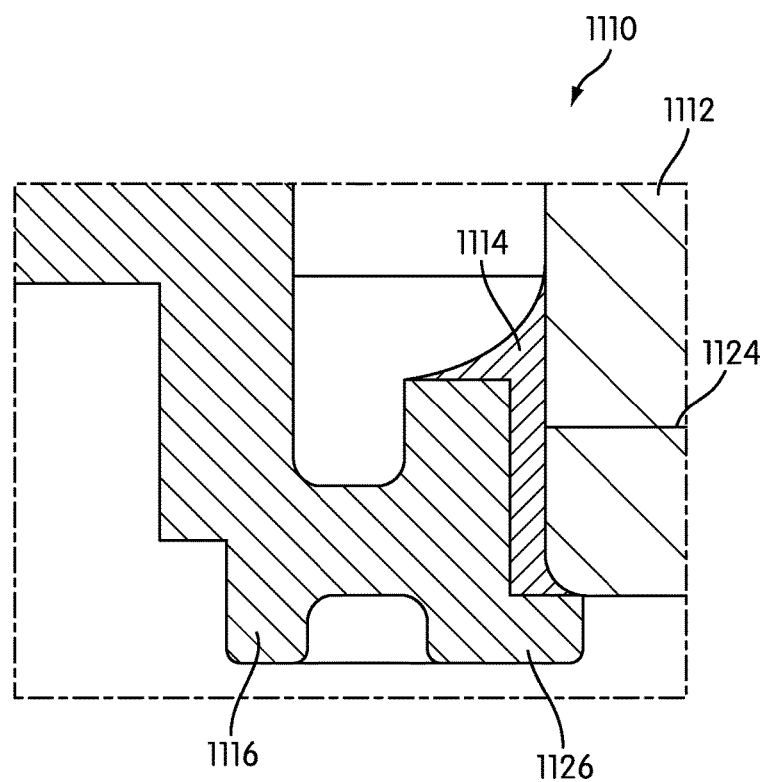
FIG. 7 is a sectional view of the portion of the medical device of FIG. 4, taken along area 7 as shown in FIG. 6.

Referring to FIGS. 6-7, the feedthrough 1112 includes conductive conduits 1120 (e.g., via) extending through an insulator 1122, between top and bottom surfaces of the feedthrough 1112. In some embodiments, at least one of the conductive conduits 1120 extends partially through the insulator 1122, and couples to a horizontal conduit 1124 (FIG. 7) that extends laterally to a side of the feedthrough 1112. In other embodiments, a conduit may extend fully through a feedthrough, such as from a top to a bottom and still connect horizontally to another body. In FIG. 7, the horizontal conduit 1124 extends to the ring 1114, brazed between the ferrule 1116 and feedthrough 1112. Accordingly, the horizontal conduit 1124 may serve as a ground plane for the feedthrough 1112. In some embodiments, the conductive conduits 1120, including the horizontal conduit 1124, include platinum. In some such embodiments, the horizontal conduit 1124 is printed onto a layer of un-fired (e.g., green) ceramic material, and co-fired with the other conductive conduits 1120 and insulator 1124.

Figure 8:
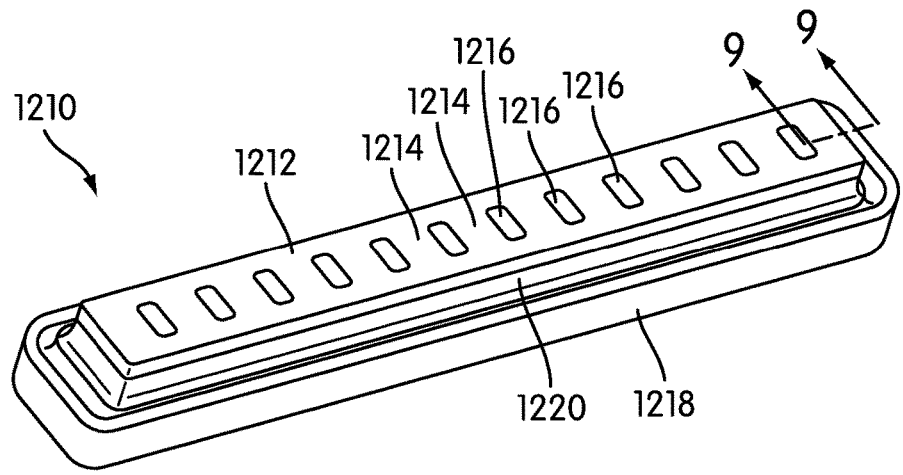
FIG. 8 is a perspective view of a portion of a medical device according to yet another exemplary embodiment.
Figure 9:
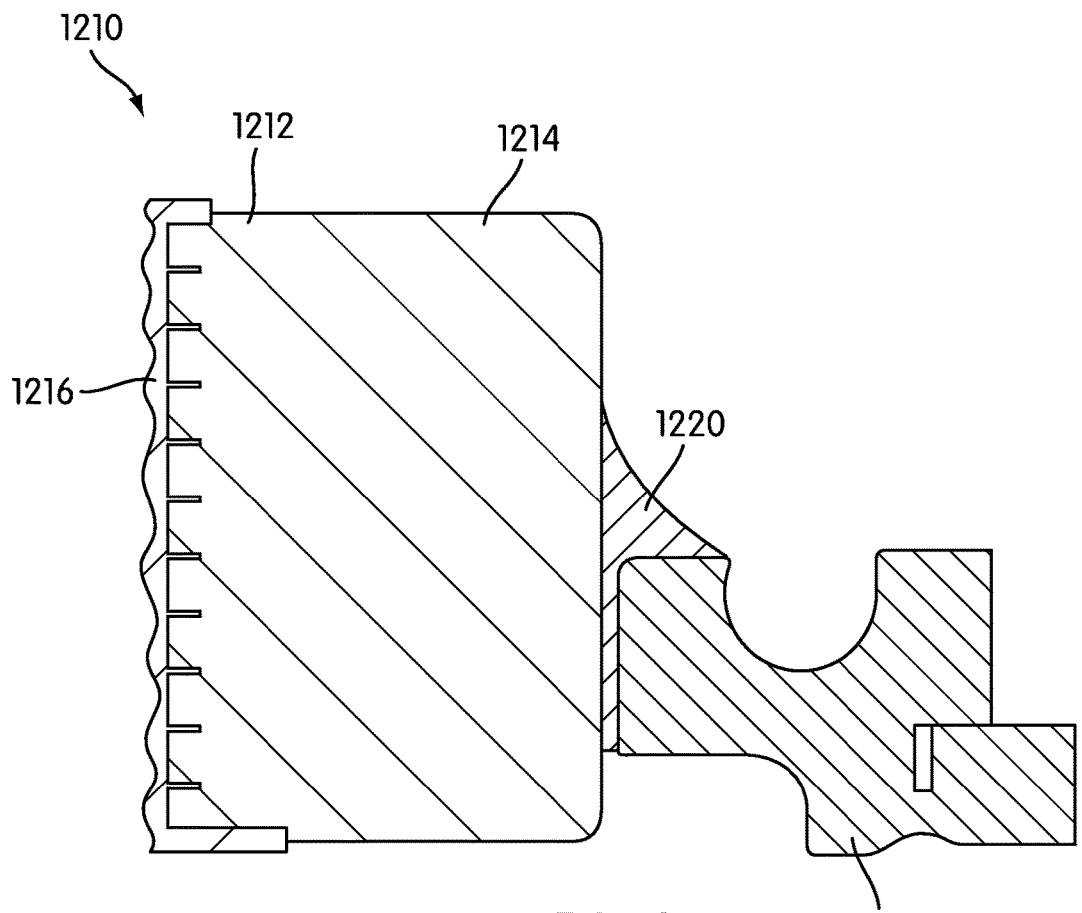
FIG. 9 is a sectional view of the portion of the medical device of FIG. 8, taken along line 9-9 as shown in FIG. 8.

Referring to FIGS. 8-9, a co-fired feedthrough 1212 includes a substantially rectangular insulator body 1214 with conductive conduits 1216. The feedthrough 1212 has been brazed into a ferrule 1218 of an implantable medical device 1210 with a ring 1220 of a biocompatible material. The prismatic shape of the rectangular insulator body 1214 (FIG. 8) is believed to improve the braze joint stability, as discussed in more detail below. According to an exemplary embodiment, the ferrule 1218 is ledge-less, where the insulator body is not supported by a flange or extension on the underside of the ferrule 1218, as compared to the ferrule 1116 having a ledge 1126 as shown in FIG. 7. The ledge-less design of the ferrule 1218 is intended to improve electrical isolation of the conductive conduits 1216 of the feedthrough 1212, by increasing the path length for shorting between the conductive conduits 1216 and the ferrule 1218, which is further intended to improve external interconnect access (e.g., a lead coupled to the feedthrough 1212).

Figure 10:
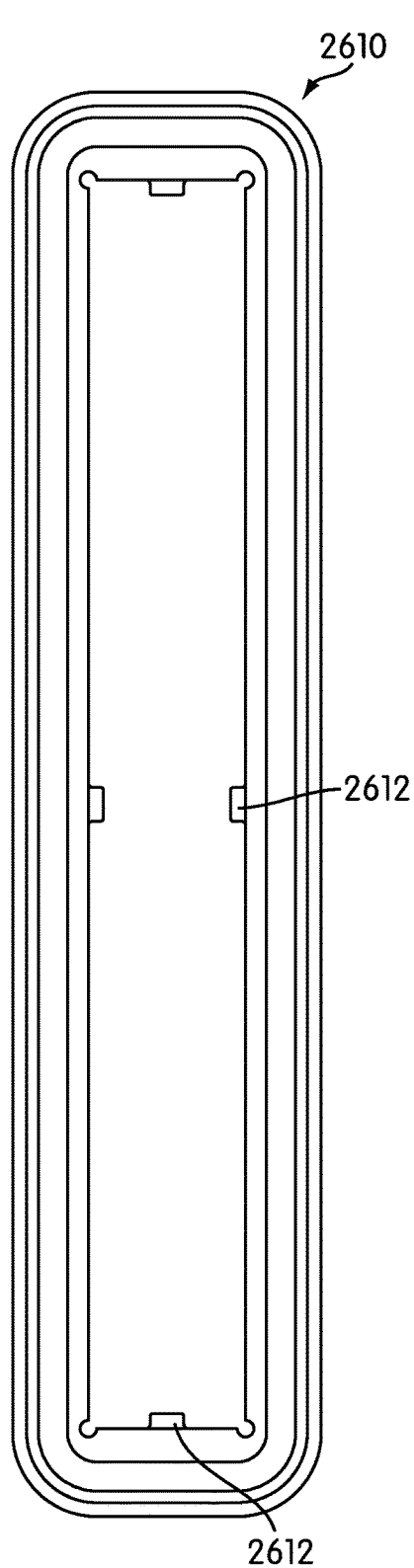
FIG. 10 is a top view of a ferrule according to an exemplary embodiment.
Figure 11:
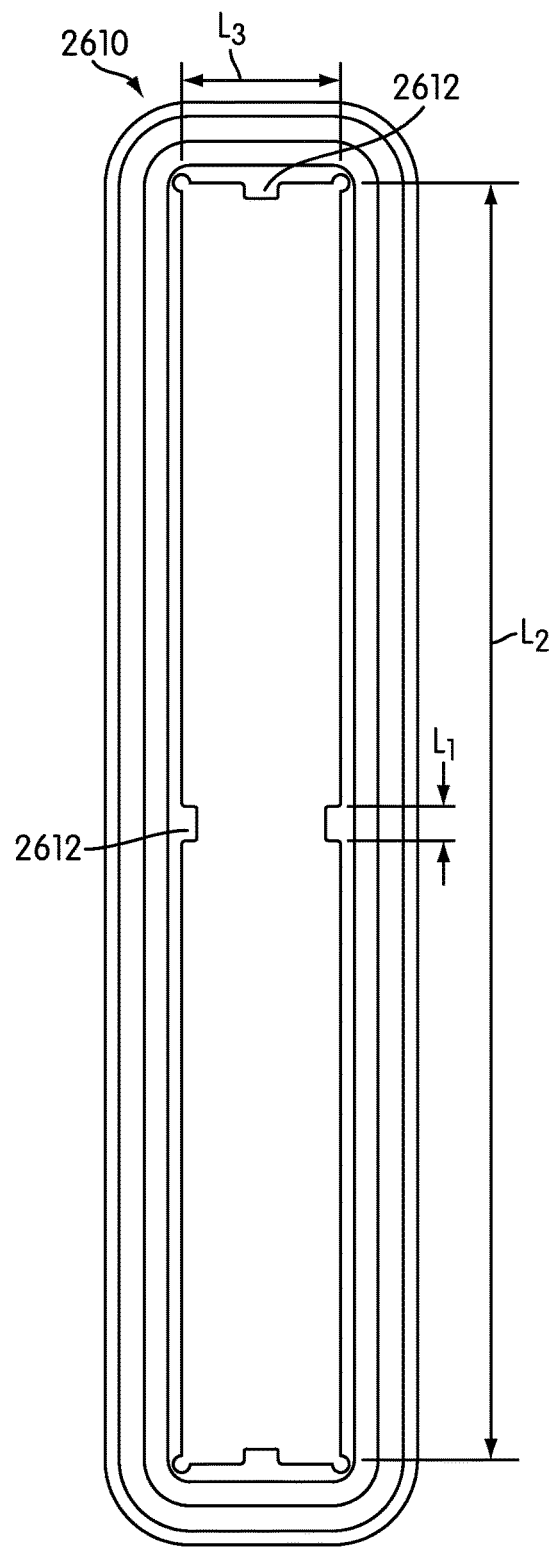
FIG. 11 is a bottom view of the ferrule of FIG. 10.

Referring to FIGS. 10-11, a ferrule 2610 for an implantable medical device is configured to receive a feedthrough. The ferrule 2610 is partially ledge-less, having tabs 2612 or other extensions positioned to receive the underside or top side of the feedthrough at isolated locations around the interior perimeter 2614 of the ferrule 2610. The size, shape, and number of the tabs vary in the same ferrule, and may vary from the geometry of the tabs 2612 in FIGS. 10-11 in different embodiments. In some embodiments, the length $L_1$ of the tabs may be less than a tenth of the length $L_2$ of the associated side, or less than a quarter of the length $L_3$ of the associated end.

In some embodiments, the tabs 2612 are positioned on the ferrule 2610 at locations that are isolated from pads on the associated feedthrough to provide the a strong dielectric breakdown between the pads and ferrule 2610. Although shown in the center of the respective interior sides of the ferrule 2610 in FIGS. 10-11, in other contemplated embodiments, tabs may extend from the corners, from only two sides, two or more from the same side, etc.

Figure 12:
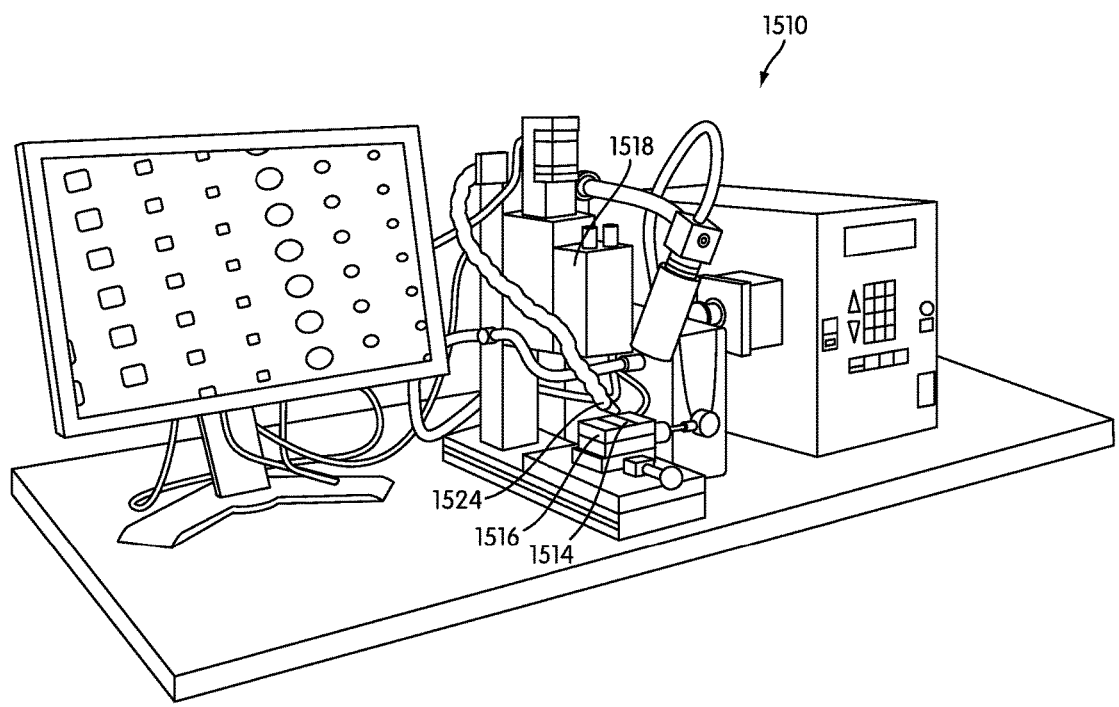
FIG. 12 is a perspective view of an assembly station according to an exemplary embodiment.

Referring to FIG. 12, a station 1510 for welding a lead 1512 (e.g., wire lead, ribbon; see FIG. 13) to a feedthrough 1514 includes a support 1516 for holding the feedthrough 1514 and a machine 1518 (e.g., robotic arm). According to an exemplary embodiment, to attach lead 1512 to a pad 1520 on the feedthrough 1514, the machine 1518 is configured to perform laser welding. In an alternative embodiment, the machine 1518 is configured to perform parallel gap welding, or another form of welding, as discussed below.

During operation, the lead 1512 is welded to the pad 1520, which overlays and is electrically coupled to a conductive via (see, e.g., conductive conduits 1120 as shown in FIG. 6) that is integrated within an insulator 1522 (FIG. 13) of the feedthrough 1512. According to an exemplary embodiment, the welding machine includes a working element 1524, such as a laser, or electrodes that direct an electric current between one another and through a portion of the lead 1512. The working element 1524 of the machine 1518 melts a portion of the lead 1512 together with the underlying pad 1520, welding the lead 1512 to the pad 1520. While FIG. 12 shows the machine 1518 with the single working element 1524, in other embodiments larger machines or groups of machines may be used. In still other contemplated embodiments, humans may manually weld leads to the feedthrough.

According to an exemplary embodiment, the leads 1512 are formed from a biocompatible material configured to be integrated with an implantable medical device. In some such embodiments, the leads 1512 are niobium. In other embodiments, the leads 1512 are a nickel alloy, such as an alloy including nickel and cobalt or an alloy including nickel, cobalt, and chromium (e.g., about 35% nickel, 35% cobalt, 20% chromium, and 10% molybdenum; 1440° C. melting point; 12.8 µm/(m·° C.) coefficient of thermal expansion). In still other embodiments, other biocompatible materials may be used such as platinum, platinum-iridium alloy, titanium, tantalum, niobium, gold, niobium, palladium, nickel, and oxides and alloys thereof It has been found that nickel alloy, such as the alloy including nickel, cobalt, and chromium, may have a relatively low melting point and exhibit a generally good biostability, when compared to other biocompatible lead materials. Platinum was further found to be useful for feedthrough pad and via material due to the biocompatibility of platinum and the coefficient of thermal expansion of platinum being commensurate with that of alumina, which may be generally used as insulator material for a feedthrough.

Figure 13:
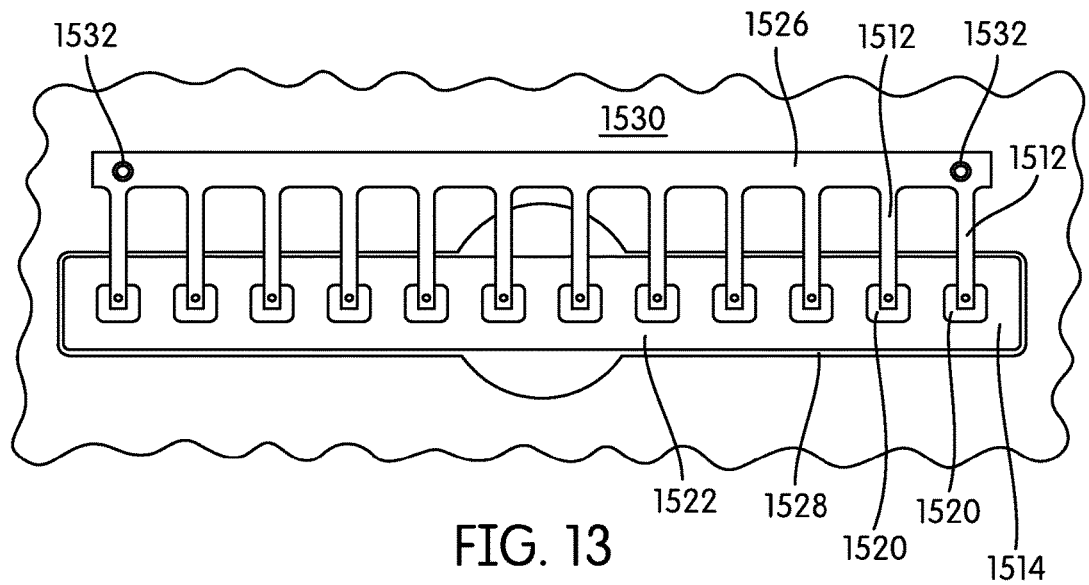
FIG. 13 is a perspective view of a lead frame and a feedthrough prior to bonding according to an exemplary embodiment.
Figure 14:
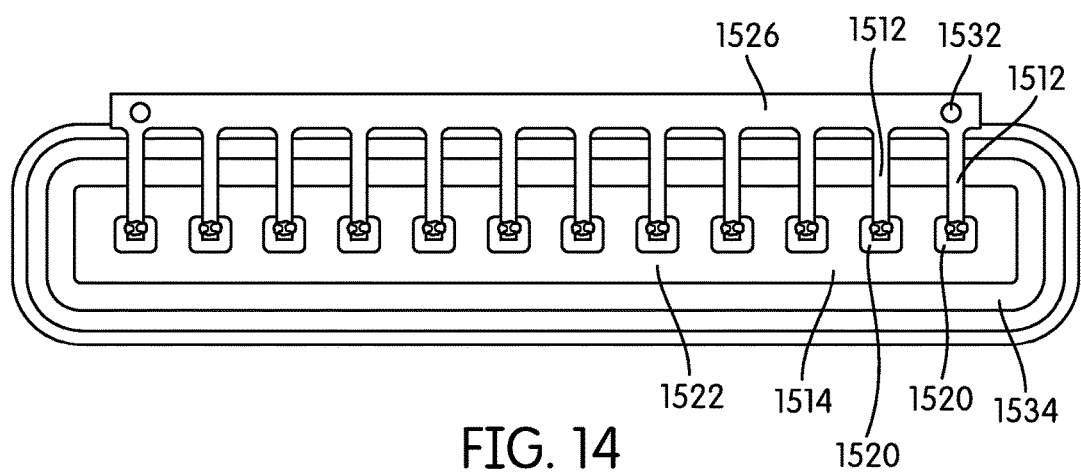
FIG. 14 is a perspective view of a lead frame bonded to a feedthrough integrated into a ferrule according to an exemplary embodiment.
Figure 15:
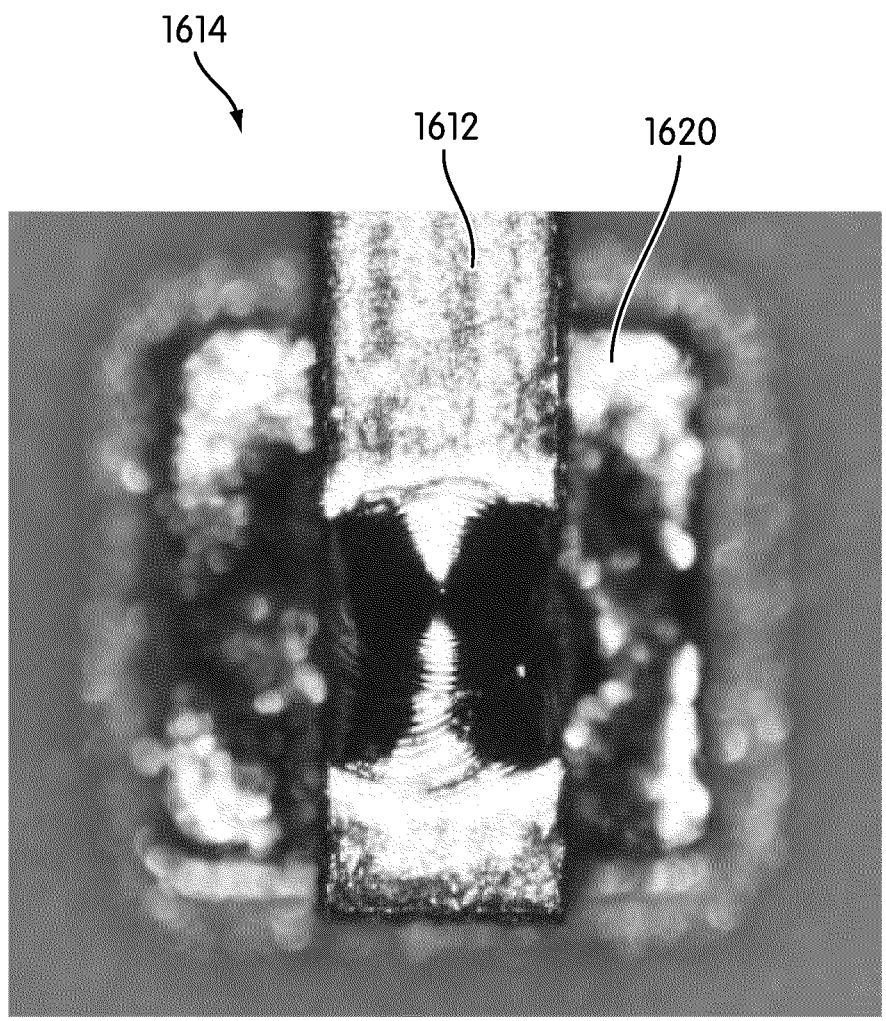
FIG. 15 is a top view of a lead welded to a pad of a feedthrough according to an exemplary embodiment.
Figure 16:
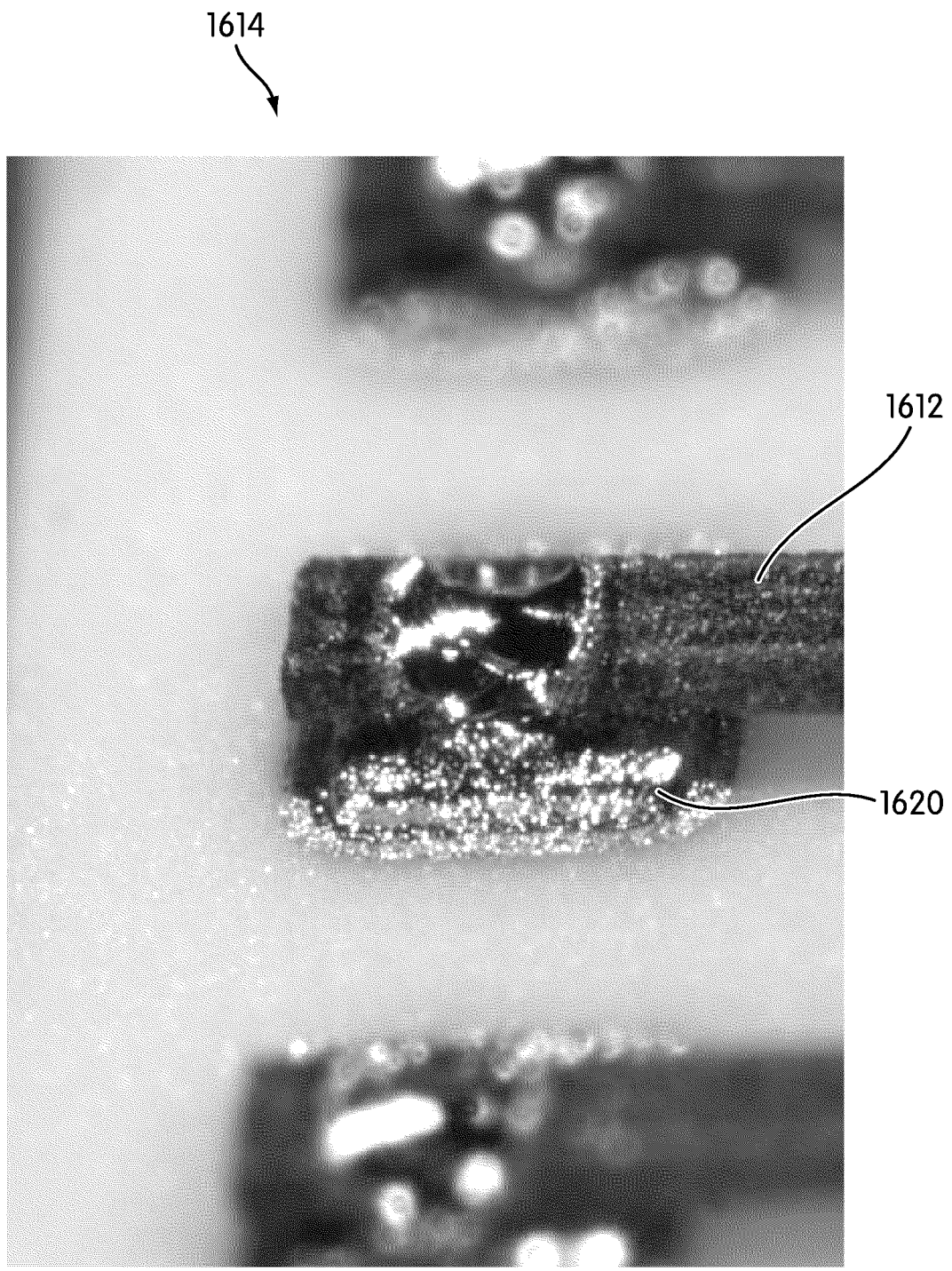
FIG. 16 is a perspective view of leads welded to pads of a feedthrough according to an exemplary embodiment.

Referring to FIGS. 13-16, a lead frame 1526 is positioned in FIG. 13 over the feedthrough 1514, with individual leads 1512 positioned over pads 1520, where each pad 1520 is associated with an underlying via (see, e.g., conductive conduits 1120 as shown in FIG. 6) integrated with the insulator 1522 of the feedthrough 1514. In some embodiments, the feedthrough 1514 is held (e.g., constrained) in a recess 1528 of a fixture 1530 and apertures 1532 in the lead frame 1526 are pinned to the fixture 1530 such that the leads 1512 are aligned with the pads 1520 of the feedthrough 1514. The machine 1518 (e.g., welding machine, joining machine, laser welding machine, resistance-based welding machine) may then be used to weld the individual leads 1512 to the respective underlying pads 1520, as shown in FIGS. 14-16. As shown in FIG. 14, leads 1512 formed from an alloy including nickel, cobalt, and chromium have been laser welded to the feedthrough 1514, and the feedthrough 1514 is integrated with a ferrule 1534. As shown in FIGS. 15-16, niobium leads 1612 have been laser welded to pads 1620 of a feedthrough 1614.

According to an exemplary embodiment, leads 1512 of the lead frame 1526 (FIG. 13) are sized to conduct a sufficient amount of electricity with relatively low resistance, while sized small enough not to fill a significant volume or provide a large weight for an implantable medical device. In some embodiments, the leads 1512 have a thickness of less than 10 mils, less than 5 mils, or about 4 mils. In some embodiments, the leads 1512 have a width of less than 30 mils, less than 25 mils, less than 12 mils, or about 24, 20, 16, or 12 mils.

For purposes of context, a set of sample feedthroughs were prepared using leads or ribbons (parallel gap or laser welded) formed from either niobium or an alloy including nickel, cobalt, and chromium. Following both laser welding and parallel gap welding, all of the samples were visually inspected and tested for weld strength. The alloy, in both lead and ribbon materials, exhibited consistent performance, showing sufficient strength without process-related damage to the pad-to-insulator interface. Overall, the results showed sufficient strength without process-related damage to the pad-to-insulator interface using either conductors formed from the alloy or niobium joined to the pad surface by either laser or parallel gap welding.

In contemplated embodiments, a variety of joining techniques may be used to form a high-strength, immersion-stable, conductive joint of a lead to an interface of a feedthrough, such as a platinum pad of a high-temperature co-fired ceramic feedthrough. Joining techniques for providing a biocompatible, biostable, reliable joint include those using heat sources, such as parallel gap welding, laser welding or otherwise joining with a laser (e.g., laser brazing, laser soldering, laser chemical reaction, laser softening of glue), opposed gap welding, step gap welding, diffusion bonding (pressure and temperature), braze or solder in a furnace, braze or solder with resistance heating, braze or solder with a laser, ultrasonic bonding, weld/ball/ribbon welding, reaction welding, sintering, and exothermic reaction of a multilayer stack. Mechanical joining techniques for establishing an electrical contact may include scraping, pressure contact, and pin and socket.

In contemplated embodiments (see generally FIGS. 35-46), an interposer such as a thin film, a thick film, or elements such as blocks, lead frames, or a stack of an additional co-fired part, joined with gold braze or platinum-sintered co-fired pads (or of other alloys such as Pt—Ir, or other nano-sized particles of refractory biostable, biocompatible metals such as platinum, platinum-iridium alloy, titanium, tantalum, niobium, gold, and alloys and oxides thereof) may be joined to the interface of the feedthrough, such as a platinum pad of a co-fired feedthrough pad or pad array. A conductive lead (such as platinum, platinum-iridium alloy, titanium, tantalum, niobium, gold, and alloys and oxides thereof) may be subsequently welded to the interposer using a variety of joining techniques to form a high-strength, immersion-stable, conductive joint of the interposer to an interface of a feedthrough, such as a platinum pad of a high-temperature co-fired ceramic feedthrough. Joining techniques for providing a biocompatible, biostable, reliable joint from pad to interposer include those using heat sources, diffusion bonding (pressure and temperature), brazing or soldering in a furnace, brazing or soldering with resistance heating, brazing or soldering with a laser or otherwise joining with a laser, ultrasonic bonding, reaction welding, and exothermic reaction of a multilayer stack.

In contemplated embodiments, hybrid approaches that combine joining techniques may be used to form a high-strength, immersion-stable, conductive joint of a lead to an interface of a feedthrough, such as a platinum pad of a high-temperature co-fired ceramic feedthrough. Primary joining techniques for providing a biocompatible, biostable, reliable, joint include those using heat sources, such as parallel gap welding, laser welding or otherwise joining with a laser, opposed gap welding, step gap welding, diffusion bonding (pressure and temperature), brazing or soldering in a furnace, brazing or soldering with resistance heating, brazing or soldering with a laser, ultrasonic bonding, weld/ball/ribbon welding, reaction welding, exothermic reaction of a multilayer stack. Mechanical joining techniques for establishing an electrical contact may include scraping, pressure contact, and pin and socket. Secondary techniques include heat treating the primary joint in a furnace, passing electrical current through the primary joint in order to promote fusion of the materials, or a combination of such techniques.

In some particular embodiments, parallel gap welding of a lead formed from an alloy including nickel, cobalt, and chromium to a platinum pad may be conducted without damaging hermeticity of the pad-to-insulator interface by using a current of less than 0.5 kA (e.g., about 0.13 kA), a force of less than five pounds per electrode (e.g., about 2 lb. force/electrode), using copper-based metal matrix composite alloy (e.g., Glidcop) electrodes (e.g., sized 0.015 by 0.025 inch), and in an inert cover gas (e.g., argon, helium, nitrogen, etc.). Such parallel gap welding may further benefit from a pad having a sufficient thickness and surface area.

During experimental testing, it was found that delamination of the via from the surrounding insulator material may occur as a result of the joining process. Such delamination may provide a leak path for bodily fluid. After recognizing the problem, it was found that the thickness of the pad or use of an interposer may be an important parameter for providing the ability to join a ribbon or wire to the pad without delamination occurring. It is believed that a minimum thickness of the pad or interposer allows for thermal management of heat generated in parallel gap welding or other joining processes, which mitigates damage to the underlying ceramic and may prevent delamination of the via from the ceramic. Accordingly, it has been found that in some configurations, such as those including platinum pads in co-fired feedthroughs, a minimum pad thickness of 50 µm may provide sufficient thermal management to prevent delamination of the via, and about 75 µm may provide even better results. In other configurations, such as those using other materials, the minimum pad thickness may be more or less than 50 µm. Furthermore, the design of the lead may also be used to control the joining process.

It is also believed that top surface area of the pad may be important to the ability to join a ribbon or wire to the pad without delamination, such as delamination of the pad from the insulator, which may provide a leak path for bodily fluid. A greater top surface area of the pad may provide increased distribution of heat generated during joining, and may reduce the temperature differential and associated thermal-expansion-induced stresses along the pad-to-insulator interface. In some configurations, such as those including platinum pads in co-fired feedthroughs, it has been found that a pad having a top-surface area of at least 20×20 mil in area may be sufficient to distribute the heat, with even better results found with pads having top-surface areas of at least about 30×30 mil in area, such as 30×40 or 40×40 mil. Pads of various geometries (e.g., round, oval, etc.) having comparable surface areas may also sufficiently distribute the heat generated during joining Thermal management of the interconnect process of a feedthrough is believed important to the formation of a strong joint (e.g., between lead and pad) without imparting damage to the substrate (e.g., co-fired pad, insulator, via, and hermetic seal(s) therebetween). Excessive heat and/or loading during the interconnection joining process of the lead and pad may damage the interfaces between the pad, insulator, and via, possibly to the detriment of the hermetic seal. Lead frames, such as those shown in FIGS. 17-34, may be designed to improve the heat capacity of the joint, minimize the melt volume, and/or provide the dissipation of the heat, allowing interconnection while maintaining the hermetic seals.

According to an exemplary embodiment, sacrificial exothermic reactions may be used to facilitate for thermal management during the interconnection joining process. In some embodiments, a carbon coating in the weld zone may be applied to either the pad or lead. In other contemplated embodiments, other coatings are used to produce sacrificial exothermic reactions during the interconnection joining process.

In some embodiments, the pad is designed with increased thickness, increased thermal mass, and/or increased heat capacity, as discussed herein. Materials may be specifically selected to provide such pads, such as niobium, tantalum, platinum, titanium, gold, and alloys thereof. In contemplated embodiments, various fastening techniques may be used to construct such pads or to add mass or thickness thereto, including laser joining, sintering of additional metallization, plating, sputter film(s), and power metal deposition (e.g., thermal spraying, co-firing).

Referring now to FIGS. 17-34, lead frames 1710 (FIGS. 17-19), 1810 (FIGS. 20-22), 1910 (FIGS. 23-25), 2010 (FIGS. 26-28), 2110 (FIGS. 29-31), 2210 (FIGS. 32-34) respectively include leads 1712, 1812, 1912, 2012, 2112, 2212 coupled to and configured to be decoupled from respective cross members 1714, 1814, 1914, 2014, 2114, 2214. In other embodiments, individual leads are not coupled to a cross member. The cross members 1714, 1814, 1914, 2014, 2114, 2214 respectively include mounting holes 1716, 1816, 1916, 2016, 2116, 2216 to facilitate alignment of the lead frames 1710, 1810, 1910, 2010, 2110, 2210 during interconnection (see, e.g., FIG. 13). It should be noted that while the leads 1712, 1812, 1912, 2012, 2112, 2212 are generally rectangular in cross section, other leads or conductive members may be round in cross section (e.g., wires) or otherwise shaped, and may also include the features (e.g., notches, holes, break-away features, etc.) shown in FIGS. 17-34.

Joint design, specifically the design of lead frames, may be used, alone or in combination with a thick co-fired pad or an interposer to allow a joining process to provide sufficient weld or bond strength and to reduce thermal shock during the joining process. Various innovative features have been contemplated for the geometry of the leads 1712, 1812, 1912, 2012, 2112, 2212 to facilitate bond or weld strength and control thermal shock. In some embodiments, the geometry of the leads 1712, 1812, 1912, 2012, 2112, 2212 includes a prismatic rectangular cross section configured to provide a thermal conduit for efficiently directing the joining energy to the weld joint. In other embodiments, the lead geometry includes a round cross section (e.g., wire lead).

Referring to FIGS. 17-25, the leads 1712, 1812, 1912 respectively include holes 1718, 1818, 1918 in the leads 1712, 1812, 1912 that are configured to be aligned with the via of the corresponding feedthrough. The holes 1718, 1818, 1918 are located proximate to ends of the leads 1712, 1812, 1912 that are opposite to the respective cross-members 1714, 1814, 1914, such as within a quarter of the length of the lead 1712, 1812, 1912 to the end. In some embodiments, the holes 1718, 1818, 1918 are designed to facilitate laser welding of the leads 1712, 1812, 1912 to an interface of a feedthrough or interposer. Use of holes 1718, 1818, 1918 may increase the surface area of the leads 1712, 1812, 1912 to receive heat for bonding of the leads to pads of the corresponding feedthrough.

The holes 1718, 1818, 1918 may be sized smaller than the corresponding laser spot size, such as a hole having a 5 mil diameter for an 8 mil diameter spot. For round vias, the diameter of the holes 1718, 1818, 1918 in the leads 1712, 1812, 1912 may be about a quarter to about twice that of the via. In some embodiments, the diameter of the hole is less than half the width of the lead. In some embodiments, the hole is less than 10 mil in diameter, such as less than 8 mil. In other embodiments, the hole is square, oval, or otherwise shaped.

In laser welding or other joining processes, material of the leads 1712, 1812, 1912 adjacent to the holes 1718, 1818, 1918 may be melted and directed through the holes 1718, 1818, 1918 to the underlying interface for joining of the lead and interface. The holes 1718, 1818, 1918 allow for less energy to be used to join the lead because the joining process need only melt enough of the lead material to pass through the holes 1718, 1818, 1918 to reach the underlying interface, instead of melting material entirely through the lead in order contact molten material with the underlying interface.

Figure 20:
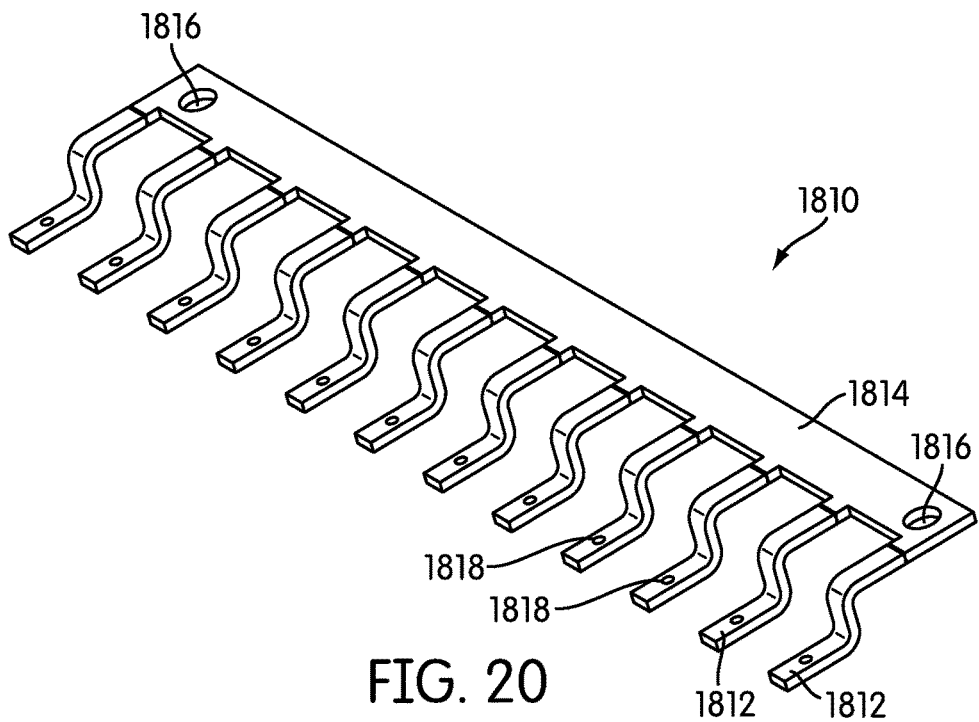
FIG. 20 is a perspective view of a lead frame according to another exemplary embodiment.
Figure 21:
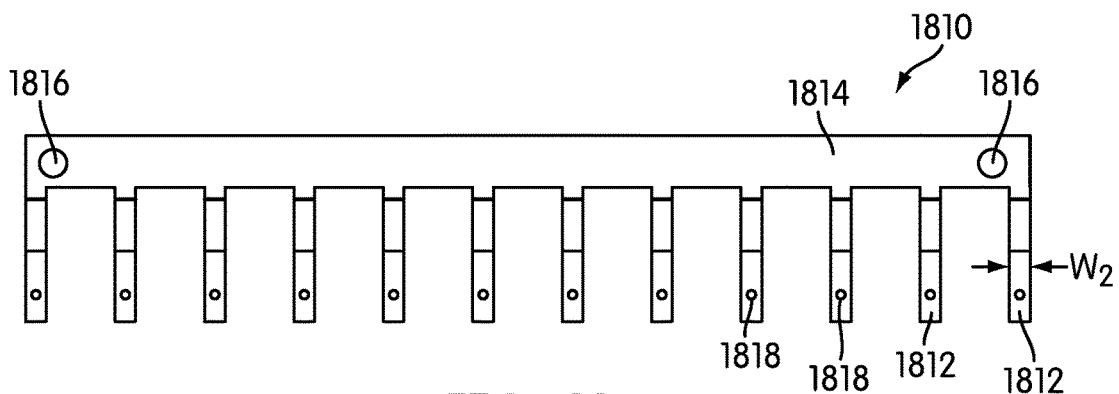
FIG. 21 is a top view of the lead frame of FIG. 20.
Figure 22:
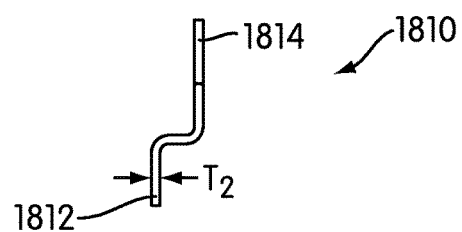
FIG. 22 is a side view of the lead frame of FIG. 20.

Referring to FIGS. 20-22, the leads 1812 of the lead frame 1810 include raised extensions that allow the leads 1812 to be fastened to a feedthrough that has been recessed into a ferrule.

Figure 17:
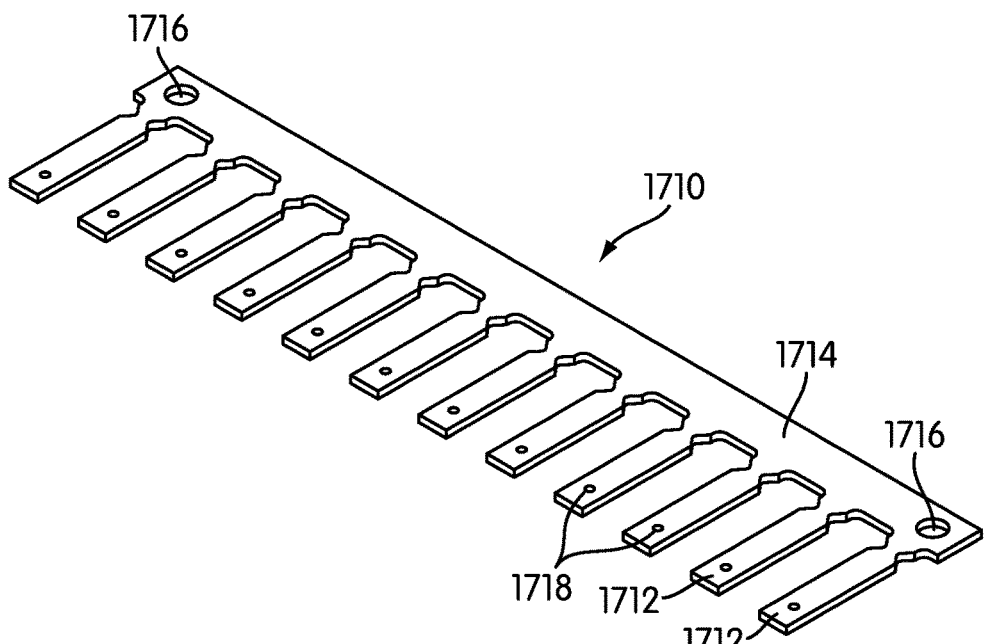
FIG. 17 is a perspective view of a lead frame according to an exemplary embodiment.
Figure 18:
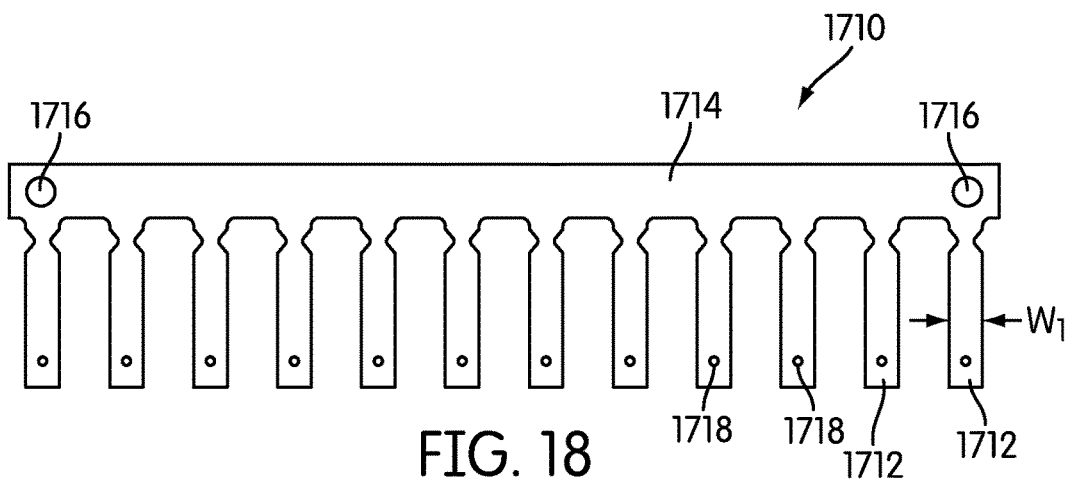
FIG. 18 is a top view of the lead frame of FIG. 17.
Figure 19:
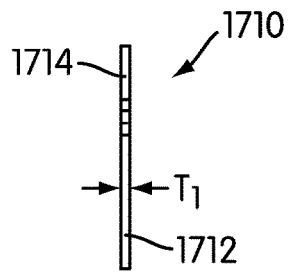
FIG. 19 is a side view of the lead frame of FIG. 17.
Figure 23:
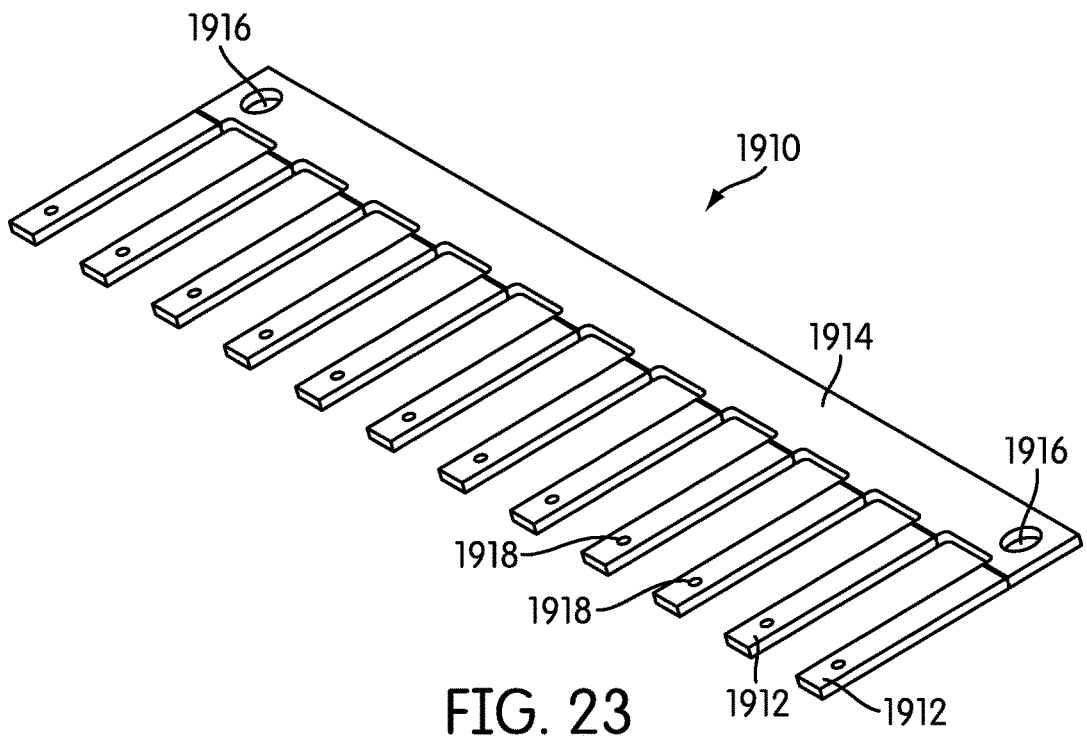
FIG. 23 is a perspective view of a lead frame according to yet another exemplary embodiment.
Figure 24:
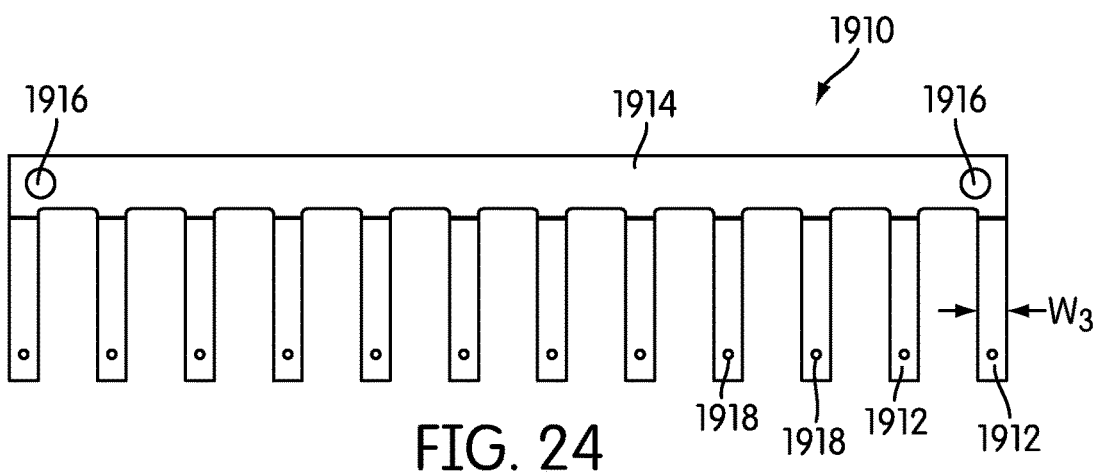
FIG. 24 is a top view of the lead frame of FIG. 23.
Figure 25:
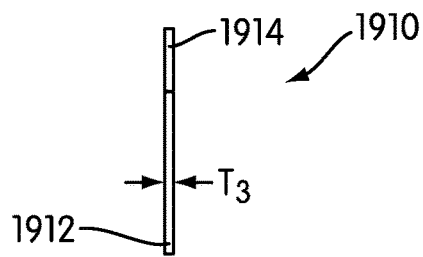
FIG. 25 is a side view of the lead frame of FIG. 23.

Referring to FIGS. 23-25, the leads 1912 have a different break-away feature than the leads 1712 in FIG. 17—scoring is used in place of narrowing. In other contemplated embodiments, combinations of break-away features may be used.

Figure 26:
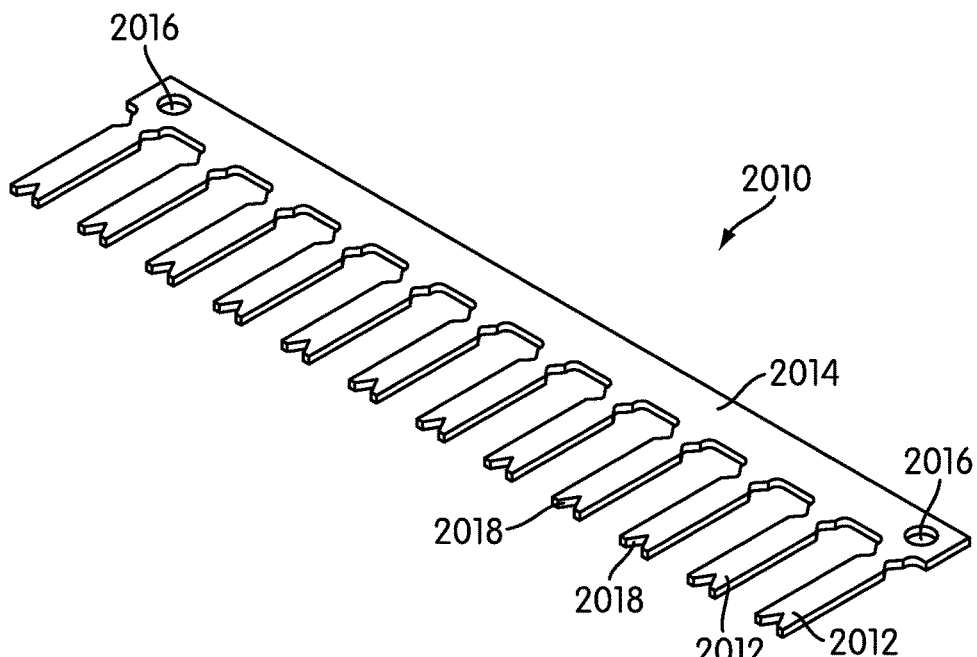
FIG. 26 is a perspective view of a lead frame according to still another exemplary embodiment.
Figure 27:
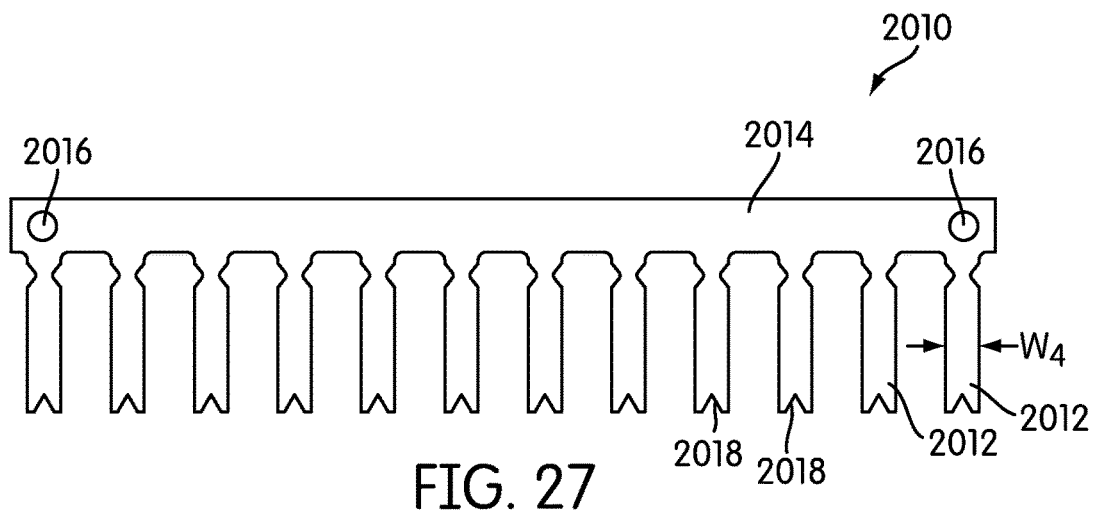
FIG. 27 is a top view of the lead frame of FIG. 26.
Figure 28:
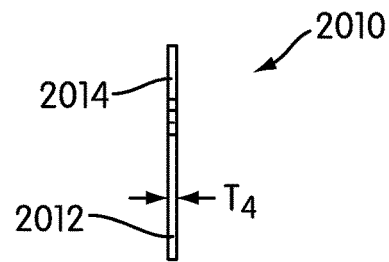
FIG. 28 is a side view of the lead frame of FIG. 26.

Referring to FIGS. 26-28, leads 2012 include a notch 2018 (e.g., V-notch or "mousebite"), which may be designed to facilitate laser welding of the leads 2012 much like the holes 1718, 1818, 1918, where the notch 2018 may be used for alignment and to provide a shortened path for molten material to reach the underlying interface. In other contemplated embodiments, shapes other than a notch or hole may be used, such as a W-shaped or U-shaped end of a lead.

Figure 29:
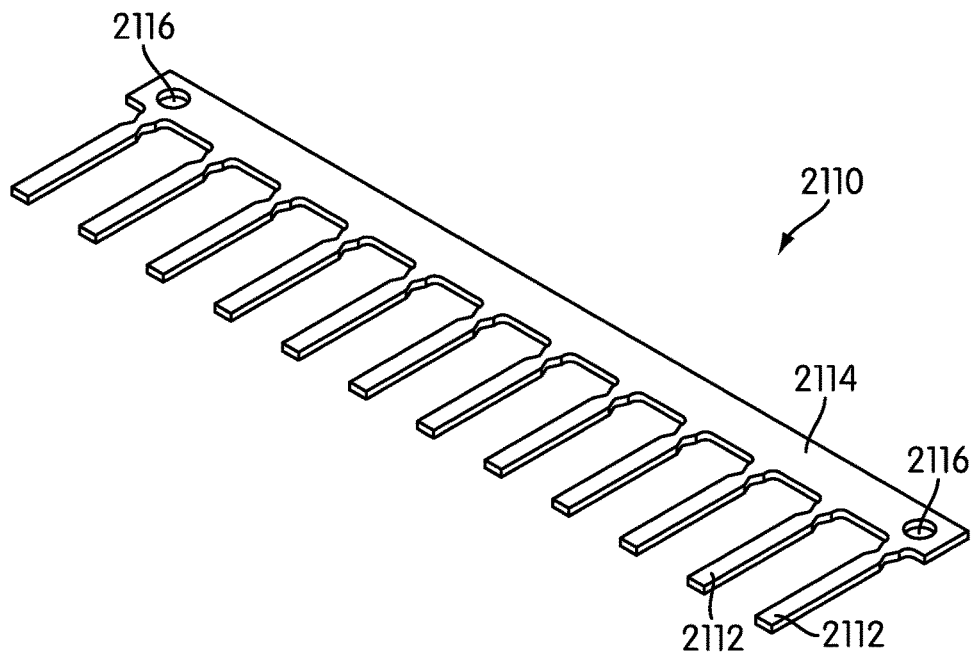
FIG. 29 is a perspective view of a lead frame according to another exemplary embodiment.
Figure 30:
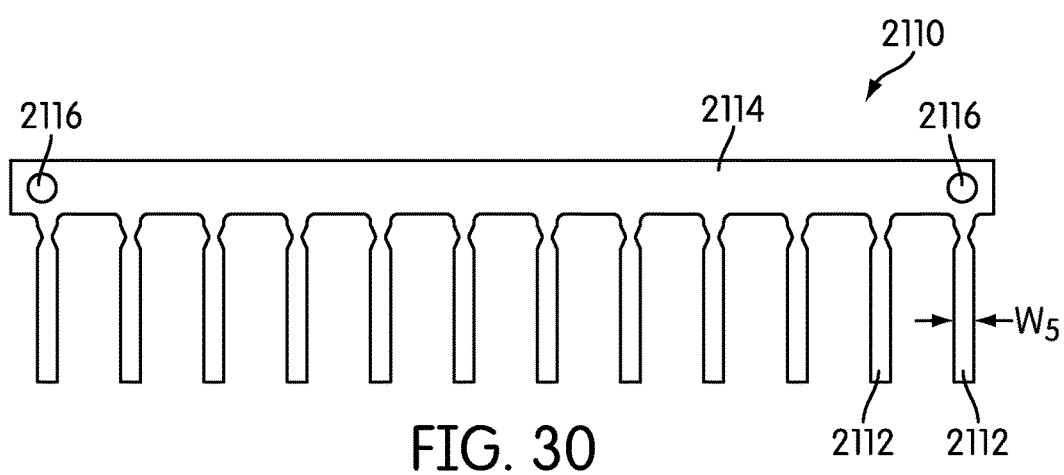
FIG. 30 is a top view of the lead frame of FIG. 29.
Figure 31:
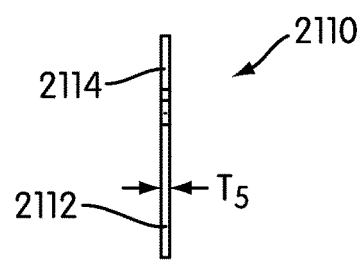
FIG. 31 is a side view of the lead frame of FIG. 29.

Referring to FIGS. 29-31, the lead frame 2110 is a simple lead frame designed for use with parallel gap welding, through-penetration laser welding, ultra-sonic bonding, or other joining techniques. The simple geometry may allow for improved repeatability with automated joining processes.

Figure 32:
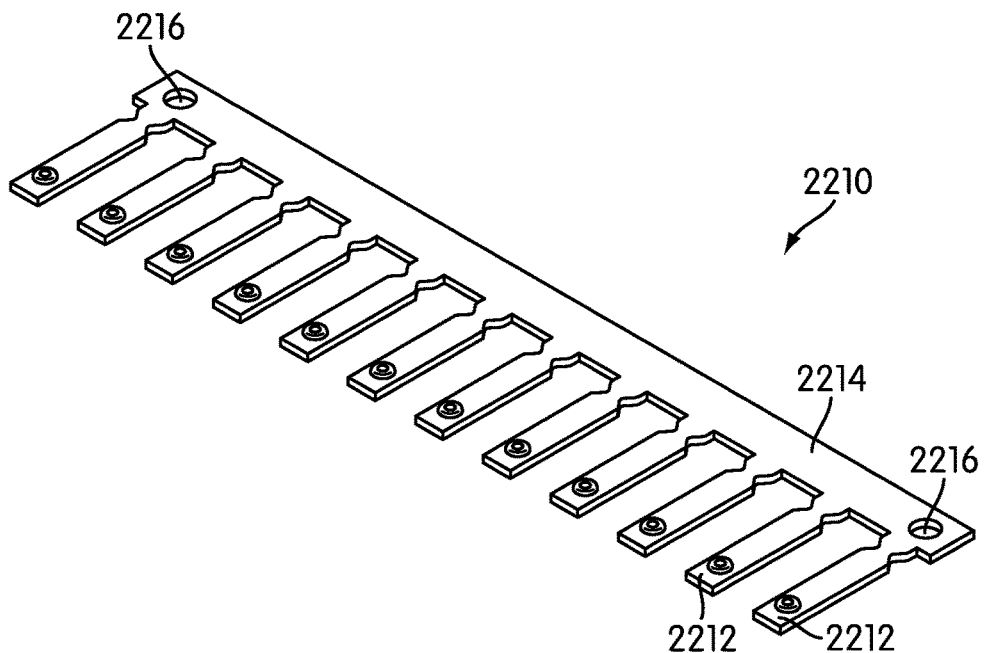
FIG. 32 is a perspective view of a lead frame according to still another exemplary embodiment.
Figure 33:
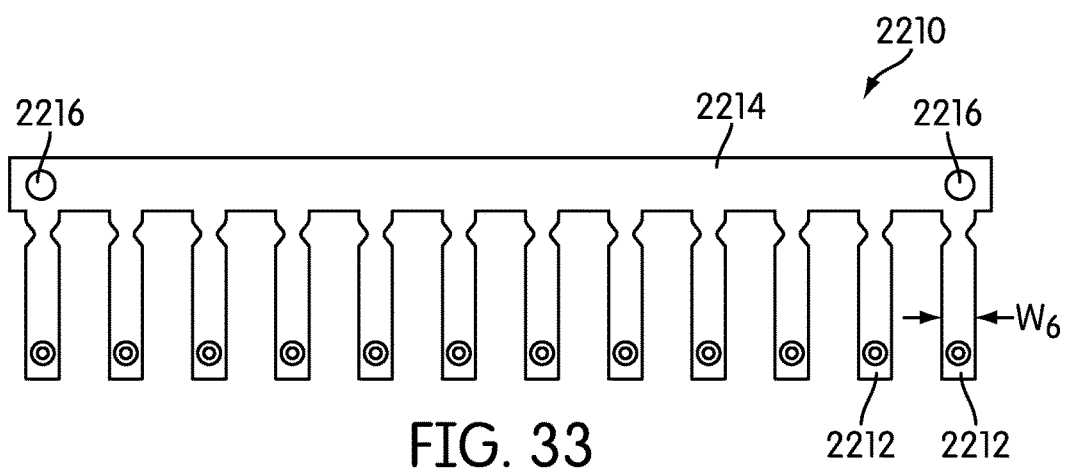
FIG. 33 is a top view of the lead frame of FIG. 32.
Figure 34:
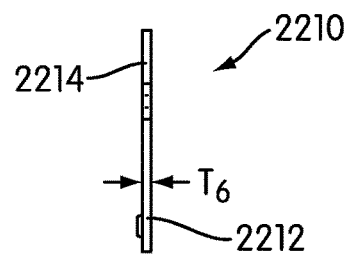
FIG. 34 is a side view of the lead frame of FIG. 32.
Figure 35:
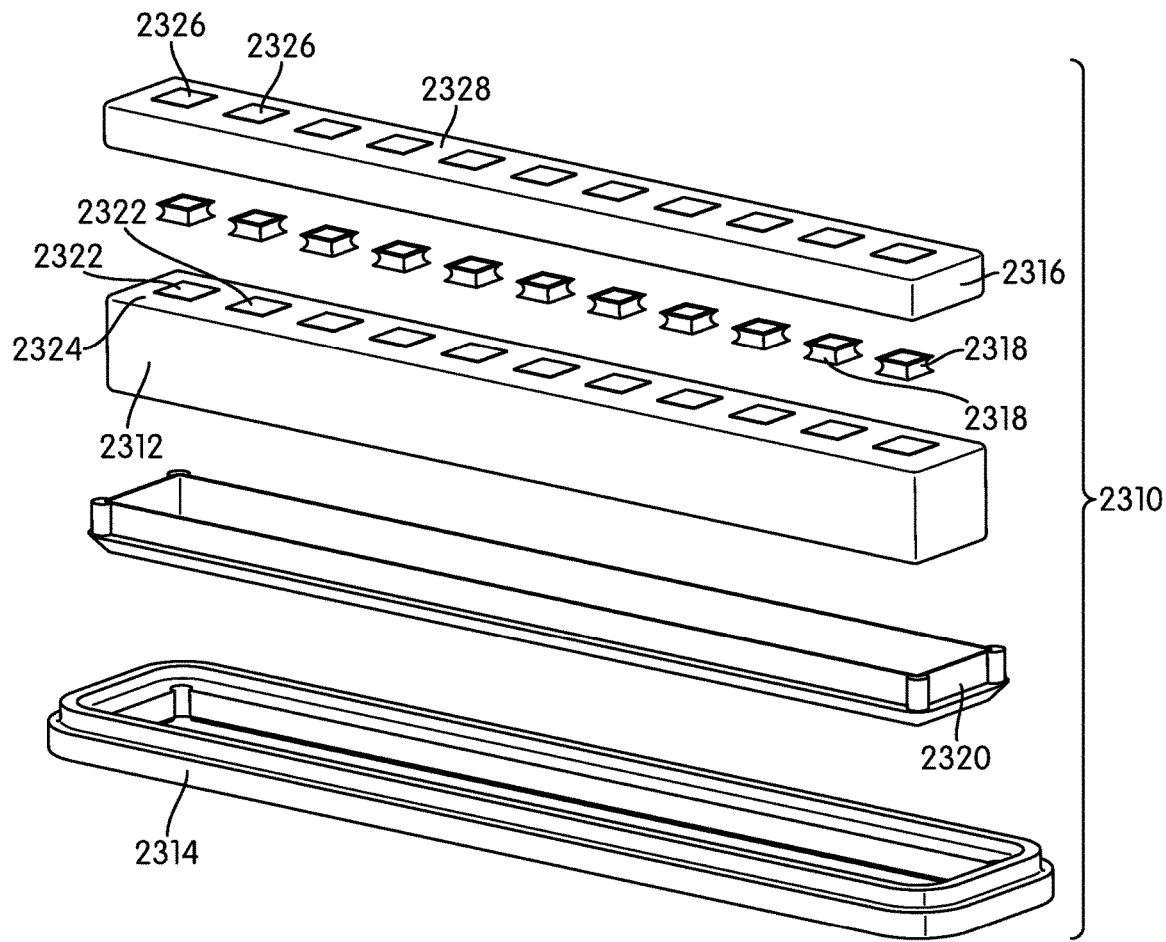
FIG. 35 is an exploded view of a feedthrough according to an exemplary embodiment.
Figure 36:
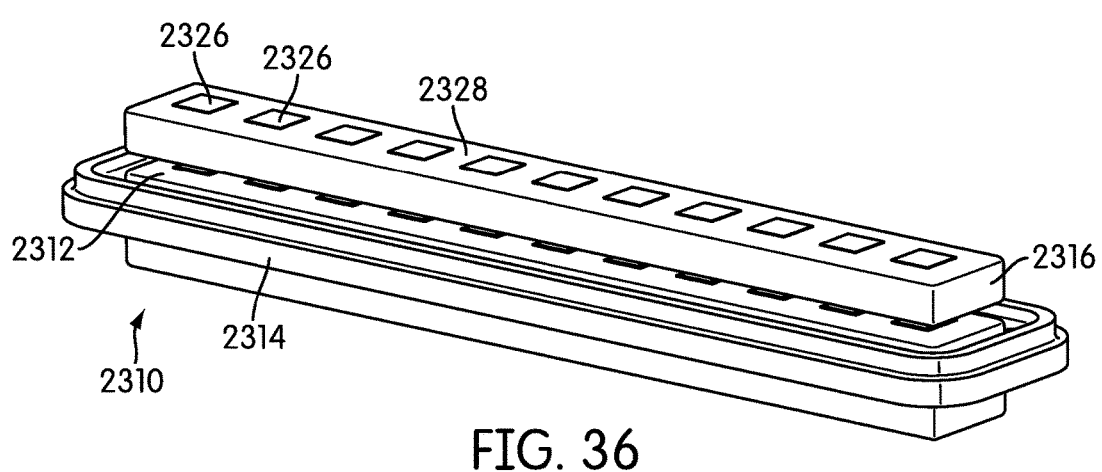
FIG. 36 is a perspective view of the feedthrough of FIG. 35.
Figure 37:
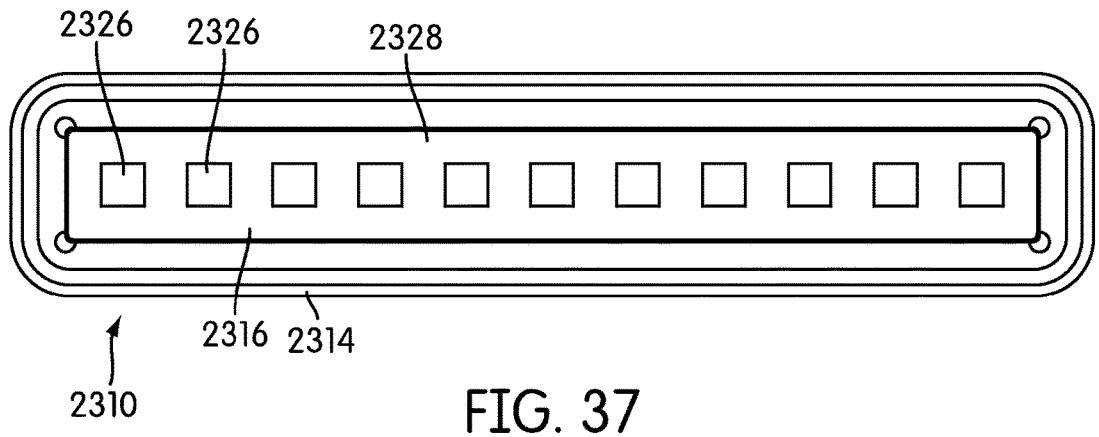
FIG. 37 is a top view of the feedthrough of FIG. 35.
Figure 38:
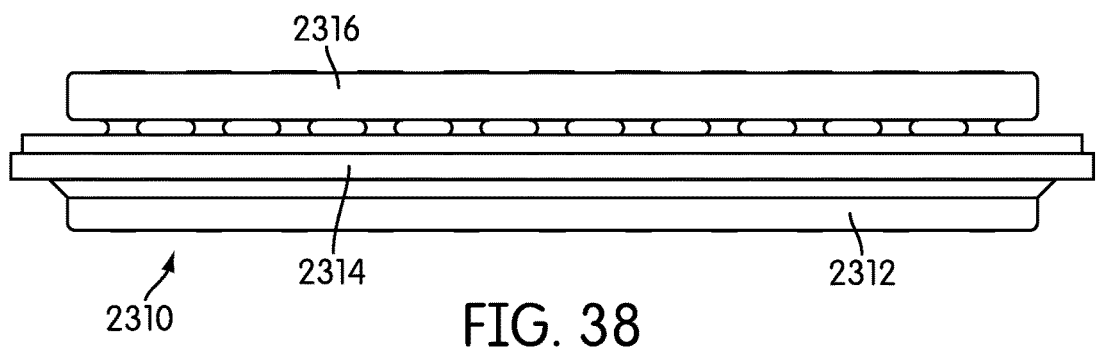
FIG. 38 is a side view of the feedthrough of FIG. 35.
Figure 39:
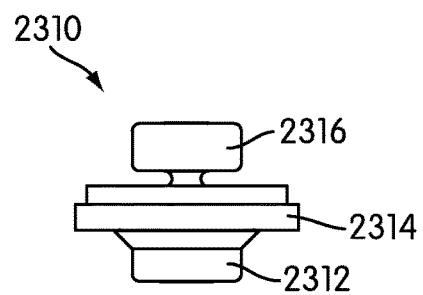
FIG. 39 is an end view of the feedthrough of FIG. 35.

Referring to FIGS. 32-34, the leads 2212 include projections 2218 (i.e., opposite side of dimple or bowl; e.g., bumps, extensions) near the ends of the leads. The projections 2218 may control heat transfer by increasing the thermal mass or thickness of the leads 2212 and/or resistance of the leads 2212. In some embodiments, the projections 2218 are placed in contact with the underlying interface of the feedthrough, and heat is applied to the backside of the projections 2218, which may be in the form of a bowl or recess. The heat melts the projection 2218 to the underlying interface forming a weld, which may then be visually inspected because the projection 2218 separates the rest of the lead 2212 from the interface of the feedthrough.

During laser welding, there is a change in the amount of laser energy reflected by the weld when the laser has melted through the projection to the underlying surface, which may serve as a feedback signal received by an optical sensor configured to then to stop the laser. In addition to use with laser welding, leads 2212 with projections 2218 may be used to focus resistance for parallel or opposed gap welding by decreasing the contact area between the lead and underlying interface, which increases resistance at the intended site of the weld.

Lead dimensions may facilitate weld or bond strength and thermal management during the joining process. In some embodiments including leads 1712, 1812, 1912, 2012, 2112, 2212 with prismatic cross-sections, the widths $W_1$, $W_2$, $W_3$, $W_4$, $W_5$, $W_6$ of leads 1712, 1812, 1912, 2012, 2112, 2212 range from the full widths of the corresponding pads (e.g., less than 20 mil, at least 20, 30, or 40 mil) to a minimum width that may be based on minimum current handling, lead material, electrical conductivity, etc. In contemplated embodiments, the thickness $T_1$, $T_2$, $T_3$, $T_4$, $T_5$, $T_6$ of the leads 1712, 1812, 1912, 2012, 2112, 2212 may range from about a tenth to about ten times that of the corresponding pad thicknesses, such as those pad thickness discussed herein. For leads having round cross sections, the diameter of the leads may range from the full width of the corresponding pad to a minimum diameter based on minimum current handling, lead material, etc.

In some embodiments, heat treatments follow the joining technique to facilitate weld or bond strength and/or reduce residual thermal stress. In one such embodiment, resistance spot welding may accompanied by subsequent heat treatment of the joint to promote inter-diffusion in the weld zone. In another such embodiment, laser welding may be accompanied by subsequent heat treatment to promote inter-diffusion in the weld zone. In still another such embodiment, ultrasonic bonding may be accompanied by subsequent heat treatment to promote inter-diffusion in the weld zone.

In other embodiments, resistance brazing is used to facilitate weld or bond strength. According to such an embodiment, a resistance heating process (opposed gap, parallel gap, step gap) may form a braze joint between the lead and pad by adding an interlayer between the lead and pad of a biostable, biocompatible material that has a melting point lower than that of the material of the pad, such as gold or an alloy of platinum for a platinum pad. In some embodiments, the interlayer may be metal foil or be formed from a metallization technique, such as sintering of additional metallization, plating, sputter film(s), and power metal deposition (e.g., thermal spraying, laser sintering, co-firing).

In still other embodiments, a laser weld may be used in combination with a powder metal filler material added in situ.

Referring now to FIGS. 35-39, part of an implantable medical device 2310 includes a hermetic feedthrough 2312 configured to be received in a ferrule 2314, and an interposer 2316 configured to facilitate interconnection of a conductor (e.g., wire, ribbon lead) to the feedthrough 2312. In some embodiments, preforms 2318, 2320 are used as brazing material during attachment of the feedthrough 2312 into the ferrule 2314 and the interposer 2316 to the feedthrough 2312. Vias (see, e.g., conductive conduits 1120 as shown in FIG. 6) extend through the feedthrough 2312 and are capped by pads 2322.

In some embodiments, the pads 2322 of the feedthrough 2312 may not be thick enough for welding or otherwise joining of a lead without delamination or loss of hermeticity of the feedthrough 2312 with the surrounding insulator 2324 (FIG. 35), and the interposer 2316 serves as an intermediary. Instead of attaching the lead directly to the feedthrough 2312, the lead is attached to the interposer 2316, which is attached to the feedthrough 2312. The interposer 2316 also includes via (see generally conductive conduits 1120 as shown in FIG. 6) capped by pads 2326 in an insulator 2328. The interposer 2316 may be brazed with the preforms 2318, co-fired with or otherwise sintered to, or otherwise attached to the feedthrough 2312 and used as a thermal barrier during interconnection of a lead.

The preforms 2318 between the interposer 2316 and feedthrough 2312 may be formed from a material that is compatible for bonding with the pads 2322 of the feedthrough, but not with the insulator 2324. Accordingly, the material does not spread between different pads 2322 and short the vias. In some embodiments, the preforms 2318, 2320 may be formed from gold and the pads 2322, 2326 may be formed from platinum. The insulators 2324, 2328 may largely include alumina. In contemplated embodiments, the ferrule 2314 may extend to support both the feedthrough 2312 and the interposer 2316.

Structurally the interposer 2316 may be similar to the feedthrough 2312—formed from an insulator 2328 and conductive conduits 2326 extending through the insulator. In some embodiments, the interposer 2316 may be half the thickness of the feedthrough 2312 or less. However, in contrast to the pads 2322 and via of the feedthrough 2312, the pads 2326 and via of the interposer 2316 need not be hermetically sealed in some embodiments. Accordingly, the interposer 2316 may be formed with different materials than the feedthrough 2312 and/or formed with less intensive manufacturing processes. In some embodiments, the interposer 2316 may be optimized for low resistance, while the feedthrough 2312 may be optimized for hermeticity and biostability.

Figure 40:
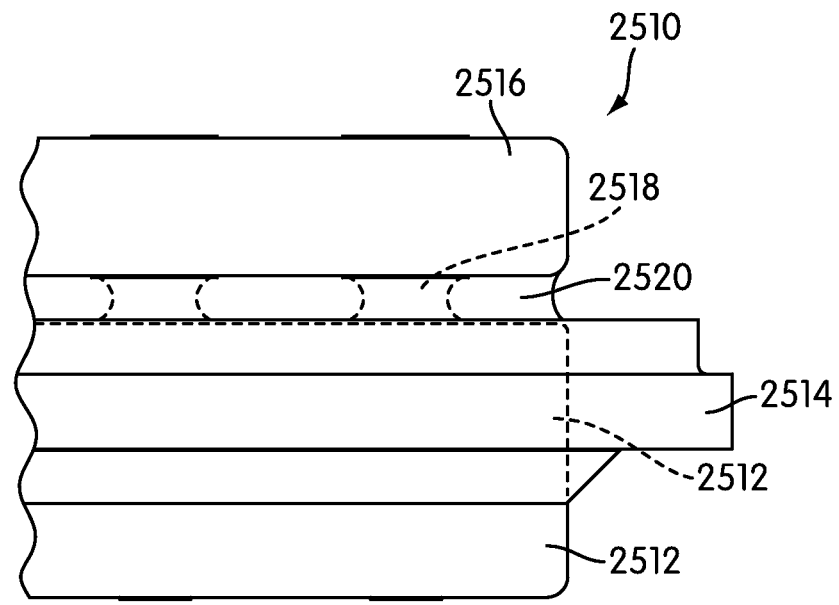
FIG. 40 is a side view of a portion of a feedthrough according to an exemplary embodiment.
Figure 41:
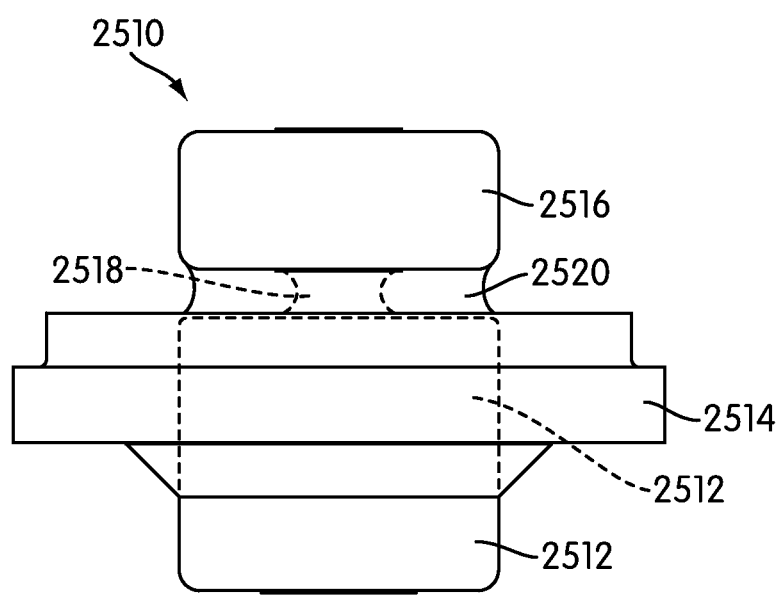
FIG. 41 is an end view of the feedthrough of FIG. 40.
Figure 42:
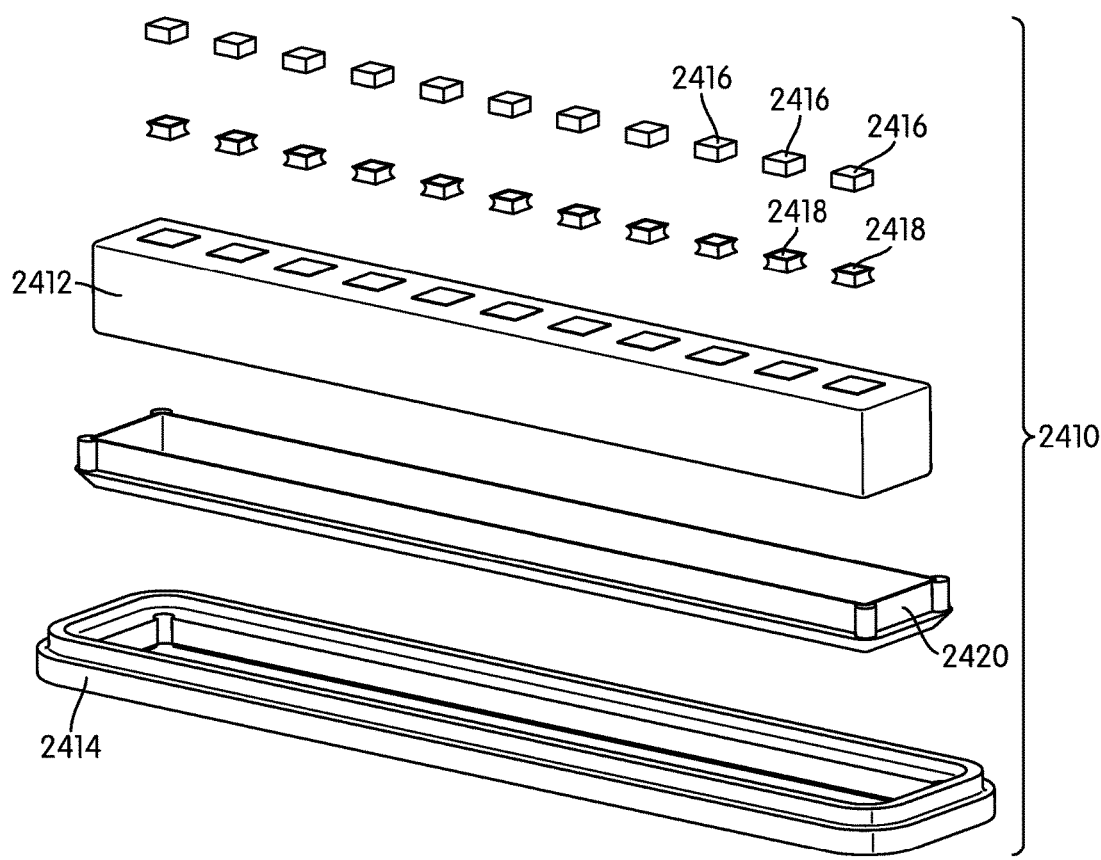
FIG. 42 is an exploded view of a feedthrough according to another exemplary embodiment.
Figure 43:
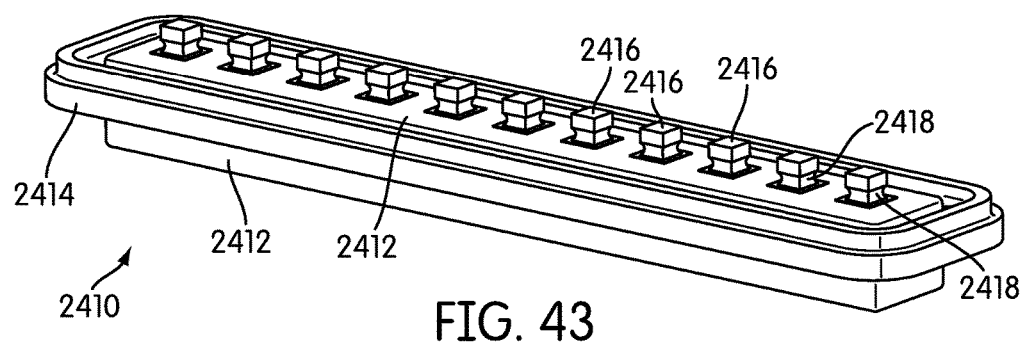
FIG. 43 is a perspective view of the feedthrough of FIG. 42.
Figure 44:
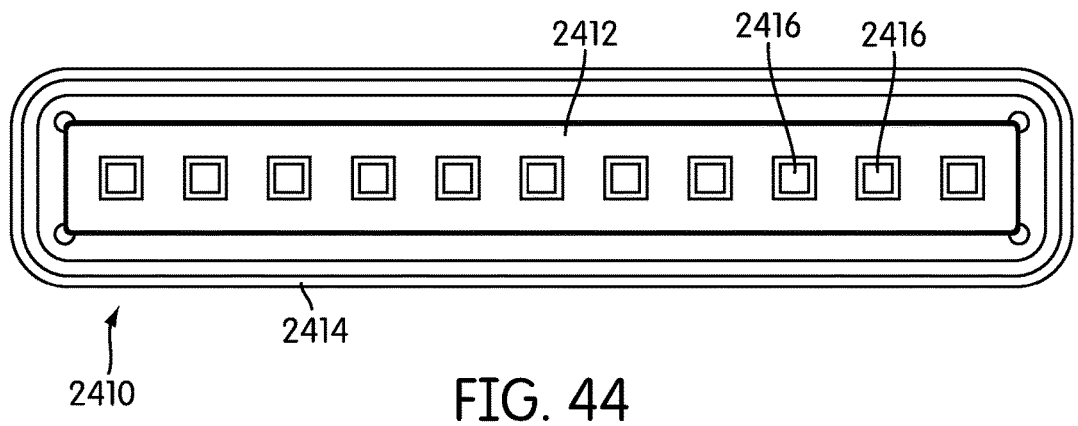
FIG. 44 is a top view of the feedthrough of FIG. 42.
Figure 45:
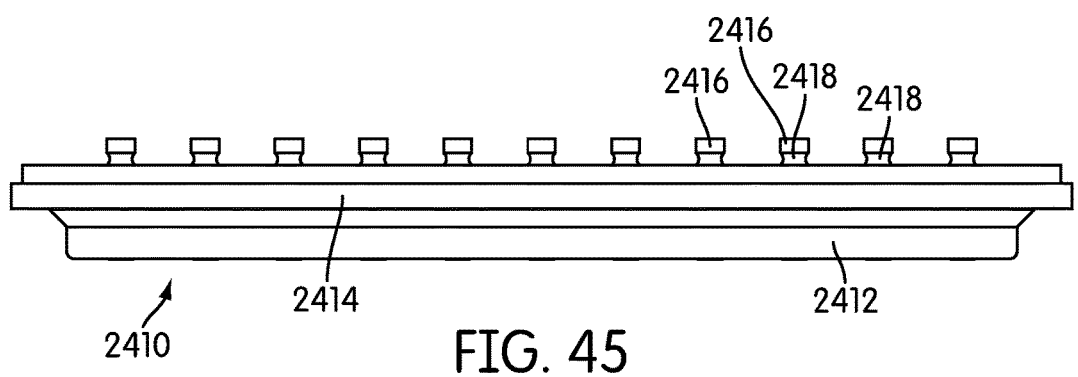
FIG. 45 is a side view of the feedthrough of FIG. 42.
Figure 46:
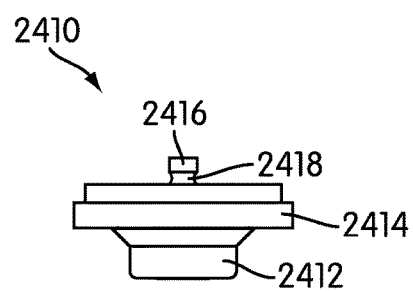
FIG. 46 is an end view of the feedthrough of FIG. 42.

Referring to FIGS. 40-41, an implantable medical device 2510, similar to implantable medical device 2310, includes a feedthrough 2512, a ferrule 2514, and an interposer 2516 coupled to the feedthrough 2512 by conductive preforms 2518 or other conductive elements coupling the interposer 2516 and the feedthrough 2512, such as extensions or pads projecting from the underside of the interposer 2516. According to an exemplary embodiment, the preforms 2518 of the implantable medical device 2510 are surrounded by a dielectric barrier 2520 (e.g., underfill) configured to provide high dielectric breakdown between preforms 2518 (and adjoining pads and via associated with either the feedthrough 2512 or interposer 2516).

According to an exemplary embodiment, the dielectric barrier 2520 is includes a material (e.g., "potting material") having a high dielectric breakdown strength. In some embodiments, the material of the dielectric barrier 2520 includes a thermoset epoxy, an ultra-violet-light-cured epoxy, a silicon-based medical adhesive, liquid silicon rubber, thermally-cured resin, other materials, or combinations thereof. In some embodiments, the dielectric barrier 2520 is applied to the implantable medical device 2510 in a liquid form contained by a mold. The dielectric barrier 2520 then fills in spaces between the preforms 2518 or other components, and cures.

Use of the dielectric barrier 2520 between the preforms 2518 for the interposer 2516 is intended to allow for a higher density of preforms, and a correspondingly higher density of conductive pads of the feedthrough coupled to the preforms 2518. The high dielectric breakdown strength may be greater than three times that of air, and in some embodiments greater than five times the dielectric breakdown strength of air. In contemplated embodiments, a similar dielectric barrier may be positioned between pads on the top or bottom of a feedthrough (e.g., pad 1216 as shown in FIG. 8), between individual-piece interposers (e.g., interposers 2416 as shown in FIGS. 42-46), or between other conductive features of implantable medical devices.

Referring to FIGS. 42-46, part of an implantable medical device 2410 includes a hermetic feedthrough 2412 configured to be received in a ferrule 2414, and interposers 2416 (e.g., blocks, pieces, caps) configured to facilitate interconnection of a conductor (e.g., wire, ribbon lead) to the feedthrough 2412. According to an exemplary embodiment, the interposers 2416 are individual conductive caps that are not held in an insulator. In some embodiments, preforms 2418, 2420 are used as brazing material during attachment of the feedthrough 2412 into the ferrule 2414 and the interposers 2416 to the feedthrough 2412.

While teachings disclosed herein relate generally to implantable medical devices (see, e.g., devices 110, 210 as shown in FIGS. 1-2), the disclosure is not intended to be limited to such devices. For example, some of the teachings disclosed herein relate to methods and structures that provide for a hermetic feedthrough, formed from a co-firing process. On a micro-scale, features that allow for a hermetic seal that remains biostable over a long duration (e.g., years), also provide strong, reliable bond between the insulator and the conductive components of the feedthrough. Such improved bond may be beneficial for non-medical, non-implantable devices undergoing conditions requiring high reliability and/or long-term hermeticity for the components of a feedthrough, such as computers that experience large changes in temperature, operate in chemically aggressive environments, electrical devices that experience relatively high vibratory loading (e.g., aircraft electronics), high-value devices robustly constructed, and other devices.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

It is important to note that the construction and arrangement of the feedthrough as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. An implantable medical device, comprising:
    an insulator of a feedthrough, the insulator having a top, a bottom, and ends and lengthwise sides that extend between the top and the bottom;
    a ferrule configured to support the insulator, wherein the ferrule comprises a frame that surrounds the ends and the lengthwise sides of the insulator, wherein the frame comprises:
        an outer extension configured to be fastened to an encasement of the implantable medical device; and
        an interior surface that faces the insulator, wherein the interior surface is mostly flat and faces the ends and lengthwise sides of the insulator and does not face a top or bottom of the insulator except for further including two or more tabs that project orthogonally from the mostly flat surface towards the insulator with the top or the bottom of the insulator being positioned against each of the two or more tabs,
    wherein the two or more tabs are straight and do not include any bend.

2. The device of claim 1 wherein the insulator is a ceramic insulator and includes a platinum via, and wherein a gold braze fastens the ceramic insulator to the ferrule.

3. The device of claim 2, wherein the gold braze contacts both the interior surface of the frame of the ferrule and the ceramic insulator of the feedthrough, but only on the ends and lengthwise sides of the ceramic insulator.

4. The device of claim 3, wherein the ferrule and the gold braze are spaced apart from top and bottom edges of the ceramic insulator.

5. The device of claim 1, wherein each of the two or more tabs are positioned at separate locations around an interior perimeter of the ferrule.

6. The device of claim 5, wherein the interior surface of the ferrule includes ends and lengthwise sides that correspond with the ends and lengthwise sides of the insulator, respectively, and lengths L3 of the ends of the interior surface of the ferrule are less than lengths L2 of the lengthwise sides of the interior surface of the ferrule; and
    wherein at least one of the tabs extends from one of the lengthwise sides of the interior surface of the ferrule and has a length L1 that is less than 1/10 of the length L2 of the lengthwise side from which it extends, L1 being measured generally parallel with L2.

7. The device of claim 5, wherein the interior surface of the ferrule includes ends and lengthwise sides that correspond with the ends and lengthwise sides of the insulator, respectively, and lengths L3 of the ends of the interior surface of the ferrule are less than lengths L2 of the lengthwise sides of the interior surface of the ferrule; and
    wherein at least one of the tabs extends from one of the ends of the interior surface of the ferrule and has a length L1 that is less than 1/4 of the length L3 of the end from which it extends, L1 being measured generally parallel with L3.

8. The device of claim 1, wherein the interior surface of the ferrule includes ends and lengthwise sides that correspond with the ends and lengthwise sides of the insulator, respectively, and at least one of the tabs extends from each the ends and lengthwise sides of the interior surface of the ferrule.

9. The device of claim 1, further comprising:
    a plurality of vias extending through the insulator; and
    a plurality of pads, each pad of the plurality of pads covering a corresponding via of the plurality of vias;
    wherein each of the two or more tabs are positioned on the ferrule at locations isolated from each pad of the plurality of pads covering the corresponding via extending through the insulator.

10. The device of claim 1, wherein the interior surface includes a first side surface that is flat and faces one of the lengthwise sides of the insulator, and a second side surface that is flat and faces another of the lengthwise sides of the insulator.

11. The device of claim 10, wherein the interior surface includes a first end surface that is flat and faces one of the ends of the insulator, and a second end surface that is flat and faces another of the ends of the insulator.

12. The device of claim 1, further comprising an encasement, wherein the outer extension of the frame of the ferrule is fastened to the encasement.

13. An implantable medical device, comprising:
    an insulator of a feedthrough, the insulator having a top, a bottom, and ends and lengthwise sides that extend between the top and the bottom;
    a ferrule configured to support the insulator, wherein the ferrule comprises a frame that surrounds the ends and the lengthwise sides of the insulator, wherein the frame comprises:
        an outer extension configured to be fastened to an encasement of the implantable medical device; and
        an interior surface that faces the insulator, wherein the interior surface is mostly flat and faces the ends and lengthwise sides of the insulator and does not face a top or bottom of the insulator except for further including two or more tabs that project from the mostly flat surface with the top or the bottom of the insulator being positioned against each of the two or more tabs,
    wherein each of the two or more tabs are positioned at separate locations around an interior perimeter of the ferrule,
    wherein the interior surface of the ferrule includes ends and lengthwise sides that correspond with the ends and lengthwise sides of the insulator, respectively, and lengths L3 of the ends of the interior surface of the ferrule are less than lengths L2 of the lengthwise sides of the interior surface of the ferrule, and
    wherein at least one of the tabs extends from one of the lengthwise sides of the interior surface of the ferrule and has a length L1 that is less than 1/10 of the length L2 of the lengthwise side from which it extends, L1 being measured generally parallel with L2.

14. An implantable medical device, comprising:
    an insulator of a feedthrough, the insulator having a top, a bottom, and ends and lengthwise sides that extend between the top and the bottom;
    a ferrule configured to support the insulator, wherein the ferrule comprises a frame that surrounds the ends and the lengthwise sides of the insulator, wherein the frame comprises:
        an outer extension configured to be fastened to an encasement of the implantable medical device; and an interior surface that faces the insulator, wherein the interior surface is mostly flat and faces the ends and lengthwise sides of the insulator and does not face a top or bottom of the insulator except for further including two or more tabs that project from the mostly flat surface with the top or the bottom of the insulator being positioned against each of the two or more tabs, wherein each of the two or more tabs are positioned at separate locations around an interior perimeter of the ferrule, wherein the interior surface of the ferrule includes ends and lengthwise sides that correspond with the ends and lengthwise sides of the insulator, respectively, and lengths L3 of the ends of the interior surface of the ferrule are less than lengths L2 of the lengthwise sides of the interior surface of the ferrule, and wherein at least one of the tabs extends from one of the ends of the interior surface of the ferrule and has a length L1 that is less than ¼ of the length L3 of the end from which it extends, L1 being measured generally parallel with L3.

15. An implantable medical device, comprising:

an insulator of a feedthrough, the insulator having a top, a bottom, and ends and lengthwise sides that extend between the top and the bottom;

a ferrule configured to support the insulator, wherein the ferrule comprises a frame that surrounds the ends and the lengthwise sides of the insulator, wherein the frame comprises:

an outer extension configured to be fastened to an encasement of the implantable medical device; and an interior surface that faces the insulator, wherein the interior surface is mostly flat and faces the ends and lengthwise sides of the insulator and does not face a top or bottom of the insulator except for further including two or more tabs that project orthogonally from the mostly flat surface towards the insulator with the top or the bottom of the insulator being positioned against each of the two or more tabs, wherein each of the two or more tabs are positioned at separate locations around an interior perimeter of the ferrule, wherein the interior surface of the ferrule includes ends and lengthwise sides that correspond with the ends and lengthwise sides of the insulator, respectively, and lengths L3 of the ends of the interior surface of the ferrule are less than lengths L2 of the lengthwise sides of the interior surface of the ferrule, and wherein at least one of the tabs extends from one of the lengthwise sides of the interior surface of the ferrule and has a length L1 that is less than ⅟10 of the length L2 of the lengthwise side from which it extends, L1 being measured generally parallel with L2.

16. An implantable medical device, comprising:

an insulator of a feedthrough, the insulator having a top, a bottom, and ends and lengthwise sides that extend between the top and the bottom;

a ferrule configured to support the insulator, wherein the ferrule comprises a frame that surrounds the ends and the lengthwise sides of the insulator, wherein the frame comprises:

an outer extension configured to be fastened to an encasement of the implantable medical device; and an interior surface that faces the insulator, wherein the interior surface is mostly flat and faces the ends and lengthwise sides of the insulator and does not face a top or bottom of the insulator except for further including two or more tabs that project orthogonally from the mostly flat surface towards the insulator with the top or the bottom of the insulator being positioned against each of the two or more tabs, wherein each of the two or more tabs are positioned at separate locations around an interior perimeter of the ferrule, wherein the interior surface of the ferrule includes ends and lengthwise sides that correspond with the ends and lengthwise sides of the insulator, respectively, and lengths L3 of the ends of the interior surface of the ferrule are less than lengths L2 of the lengthwise sides of the interior surface of the ferrule, and wherein at least one of the tabs extends from one of the ends of the interior surface of the ferrule and has a length L1 that is less than ¼ of the length L3 of the end from which it extends, L1 being measured generally parallel with L3.

* * * * *